US010016490B2

(12) United States Patent
Lu et al.

(10) Patent No.: US 10,016,490 B2
(45) Date of Patent: Jul. 10, 2018

(54) MULTIPLE-ENZYME NANOCOMPLEXES

(75) Inventors: Yunfeng Lu, Culver City, CA (US);
Ming Yan, Los Angeles, CA (US);
Yang Liu, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 839 days.

(21) Appl. No.: 14/130,873

(22) PCT Filed: Jul. 6, 2012

(86) PCT No.: PCT/US2012/045690
§ 371 (c)(1),
(2), (4) Date: Jan. 3, 2014

(87) PCT Pub. No.: WO2013/006762
PCT Pub. Date: Jan. 10, 2013

(65) Prior Publication Data
US 2014/0134700 A1     May 15, 2014

Related U.S. Application Data

(60) Provisional application No. 61/504,975, filed on Jul. 6, 2011, provisional application No. 61/529,767, filed on Aug. 31, 2011.

(51) Int. Cl.
*C12N 11/18* (2006.01)
*A61K 38/44* (2006.01)
*A61K 47/48* (2006.01)
*B82Y 5/00* (2011.01)

(52) U.S. Cl.
CPC ............ *A61K 38/443* (2013.01); *A61K 38/44* (2013.01); *A61K 47/48092* (2013.01); *C12N 11/18* (2013.01); *B82Y 5/00* (2013.01)

(58) Field of Classification Search
CPC .............. A61K 47/48092; A61K 38/44; A61K 38/443; C12N 11/18; B82Y 5/00
See application file for complete search history.

(56) References Cited

U.S. PATENT DOCUMENTS

| | | | |
|---|---|---|---|
| 4,450,153 A | 5/1984 | Hopkins | |
| 4,486,408 A | 12/1984 | Kiel | |
| 4,952,406 A | 8/1990 | Brown et al. | |
| 5,262,151 A | 11/1993 | Montgomery | |
| 6,153,217 A | 11/2000 | Jin et al. | |
| 7,056,901 B2 | 6/2006 | Frechet et al. | |
| 2009/0004278 A1 | 1/2009 | Aimi et al. | |
| 2009/0060894 A1 | 3/2009 | Somberg et al. | |
| 2009/0239324 A1 | 10/2009 | Herdt et al. | |
| 2010/0215725 A1 | 8/2010 | Schwarz et al. | |
| 2011/0008455 A1 | 1/2011 | Taralp | |

FOREIGN PATENT DOCUMENTS

| | | | | |
|---|---|---|---|---|
| EP | 0062434 | 10/1982 | | |
| WO | WO 2008105773 A2 * | 9/2008 | ........... | A61K 9/5153 |
| WO | 2010104865 | 9/2010 | | |
| WO | 2011004328 | 1/2011 | | |
| WO | 2012142410 | 10/2012 | | |

OTHER PUBLICATIONS

Xie et al., Recent advance in the support and technology used in enzyme immobilization, African Journal of Biotechnology, 2009, vol. 8, pp. 4724-4733.*
Dziubla et al., Polymer nanocarriers protecting active enzyme cargo against proteolysis, Journal of Controlled Release, 2005, vol. 102, pp. 427-439.*
Yan M. et al., "A novel intracellular protein delivery platform based on single-protein nanocapsules", Nature Biotechnology, Jan. 2010, vol. 5, pp. 48-53 (published online, Nov. 22, 2009). (Year: 2010).*
Van der Klei I. J. et al., "The significance of peroxisomes in methanol metabolism in methylotrophic yeast", Biochimica et Biophysica Acta 1763, 2006, pp. 1453-1462. (Year: 2006).*
Hnaien et al. "A rapid and sensitive alcohol oxidase/catalase conductometric biosensor for alcohol determination", Talanta, vol. 81, pp. 222-227, 2010.
Lizano et al. "Mouse erythrocytes as carriers for coencapsulated alcohol and aldehyde dehydrogenase obtained by electroporation", Life Sciences, vol. 68, No. 17, pp. 2001-2016, 2001.
Liu et al. "Biomimetic enzyme nanocomplexes and their use as antidotes and preventive measures for alcohol intoxication", Nature Nanotechnology, vol. 8, No. 3, pp. 187-192, 2013.
Chinese Office Action dated Jan. 16, 2015 from Chinese Patent Application No. 201280043352.4.
Supplementary European Search Report dated Jan. 30, 2015 from European Patent Application No. 12808075.1.
Supplementary European Search Report dated Nov. 6, 2015 from European Patent Application No. 12807431.7.
Niemeyer et al. "DNA-directed assembly of bienzymic complexes from in vivo biotinylated NAD(P)H:FMN oxidoreductase and luciferase", Chembiochem—A European Journal of Chemical Biology, No. 2-3, pp. 242-245, 2002.
Yan et al. "Encapsulation of single enzyme in Nanogel with enhanced biocatalytic activity and stability", J. Am. Chem. Soc., vol. 128, pp. 11008-11009, 2006.
Examination Report dated Jul. 12, 2016, EP Application No. 12807431.7.
Crabb et al., "Overview of the role of alcohol dehydrogenase and aldehyde dehydrogenase and their variants in the genesis of alcohol-related pathology." Proceedings of the Nutrition Society 63.01 (2004): 49-63.
Ellis, "Macromolecular crowding: obvious but underappreciated." Trends in biochemical sciences 26.10 (2001): 597-604.
Fierobe et al., "Design and production of active cellulosome chimeras Selective incorporation of dockerin-containing enzymes into defined functional complexes." Journal of Biological Chemistry 276.24 (2001): 21257-21261.
Fierobe et al., "Degradation of cellulose substrates by cellulosome chimeras Substrate targeting versus proximity of enzyme components." Journal of Biological Chemistry 277.51 (2002): 49621-49630.

(Continued)

*Primary Examiner* — Satyendra K Singh
(74) *Attorney, Agent, or Firm* — Gates & Cooper LLP

(57) ABSTRACT

Provided are nanocomplexes having at least two different enzymes and a polymeric network anchored to at least one of the enzymes. In some embodiments, the activities of the enzymes catalyze a cascade reaction.

12 Claims, 14 Drawing Sheets

(56) References Cited

OTHER PUBLICATIONS

Ji et al., "Role of TNF-α in ethanol-induced hyperhomocysteinemia and murine alcoholic liver injury." Hepatology 40.2 (2004): 442-451.
Koch-Schmidt et al., "Aspects on microenvironmental compartmentation." European Journal of Biochemistry 81.1 (1977): 71-78.
Leader et al., "Protein therapeutics: a summary and pharmacological classification." Nature Reviews Drug Discovery 7.1 (2008): 21-39.
Månsson et al., "Site-to-site directed immobilization of enzymes with bis-NAD analogues." Proceedings of the National Academy of Sciences 80.6 (1983): 1487-1491.
Mao et al., "A string of enzymes, purification and characterization of a fusion protein comprising the four subunits of the glucose phosphotransferase system of Escherichia coli." Journal of Biological Chemistry 270.31 (1995): 18295-18300.
Mingardon et al., "Exploration of new geometries in cellulosome-like chimeras." Applied and environmental microbiology 73.22 (2007): 7138-7149.
Riedel et al., "Intramolecular synergism in an engineered exo-endo-1, 4-β-glucanase fusion protein." Molecular microbiology 28.4 (1998): 767-775.
Schlesinger et al., "Pegloticase." Nature Reviews Drug Discovery 10.1 (2011): 17-18.
Selvin, "The renaissance of fluorescence resonance energy transfer." Nature structural biology 7.9 (2000).
Seo et al., "Characterization of a bifunctional enzyme fusion of trehalose-6-phosphate synthetase and trehalose-6-phosphate phosphatase of Escherichia coli." Applied and environmental microbiology 66.6 (2000): 2484-2490.
Sheldon, "Enzyme immobilization: the quest for optimum performance." Advanced Synthesis & Catalysis 349.8-9 (2007): 1289-1307.
Sherman et al., "PEG-uricase in the management of treatment-resistant gout and hyperuricemia." Advanced drug delivery reviews 60.1 (2008): 59-68.
Shibuya et al., "Construction of an alpha-amylase/glucoamylase fusion gene and its expression in Saccharomyces cerevisiae." Bioscience, biotechnology, and biochemistry 56.6 (1992): 884-889.
Srere et al., "An immobilized three-enzyme system: a model for microenvironmental compartmentation in mitochondria." Proceedings of the National Academy of Sciences 70.9 (1973): 2534-2538.
Sundy et al., "Reduction of plasma urate levels following treatment with multiple doses of pegloticase (polyethylene glycol-conjugated uricase) in patients with treatment—failure gout: Results of a phase II randomized study." Arthritis & Rheumatism 58.9 (2008): 2882-2891.
Yan et al., "Evolution of organelle-associated protein profiling." Journal of proteomics 72.1 (2009): 4-11.
PCT International Search Report and Written Opinion dated Dec. 17, 2012 for PCT Application No. PCT/US2012/045690.
Brady, D., et a., "Advances in enzyme immobilisation", Biotechnol Lett, 2009, pp. 1639-1650, vol. 31.
Cao, L., "Carrier-bound Immobilized Enzymes: Principles, Application and Design", Wiley-VCH, 2005, pp. 1-52.
Sheldon, R.A., "Enzyme Immobilization: The Quest for Optimum Performance", Adv. Synth. Catal., 2007, pp. 1289-1307, vol. 349.
Xie, T., et al., "Recent advance in the support and technology used in enzyme immobilization", African Journal of Biotechnology, 2009, pp. 4724-4733, vol. 8, No. 19.

* cited by examiner

MULTIPLE-ENZYME NANOCOMPLEXES

REFERENCE TO RELATED APPLICATIONS

This application claims the benefit under 35 U.S.C. Section 119(e) of U.S. Provisional Patent Application Ser. No. 61/504,975, filed on Jul. 6, 2011, entitled "ORAL DELIVERY OF ENZYMES BY NANOCAPSULES FOR TARGETED METABOLISM OF ALCOHOL OR TOXIC METABOLITES", and U.S. Provisional Patent Application Ser. No. 61/529,767, filed on Aug. 31, 2011, entitled "MULTIPLE-ENZYME NANOCOMPLEXES", the contents of each of which are incorporated herein by reference.

STATEMENT OF GOVERNMENT SUPPORT

This invention was made with Government support under Grant No. HDTRA1-09-1-0001, awarded by the United States Department of Defense, Defense Threat Reduction Agency. The Government has certain rights in this invention.

FIELD OF THE DISCLOSURE

This disclosure generally relates to nano-structures containing multiple enzymes that cooperatively carry out their enzymatic functions. Methods of preparing and using such structures are also disclosed.

BACKGROUND

Enzymes are exquisite biocatalysts mediating every biological process in living organisms. In eukaryote cells, most enzymes are not freely diffused within the cytosols, but are spatially defined within subcellular organelles or closely co-localized as enzyme complexes along with other proteins (see, e.g. Conrado et al., Curr Opin Biotech 19, 492-499, (2008); Yan et al., J Proteomics 72, 4-11, (2009)). In consecutive reactions catalyzed by multiple enzymes, such close confinement minimizes diffusion of intermediates among the enzymes, enhancing overall reaction efficiency and specificity (see, e.g. Yan et al., J Proteomics 72, 4-11, (2009)).

Typically in vivo, toxic intermediates generated during a metabolic process are promptly eliminated by the proximate enzymes designed to degrade such toxins and which are co-localized within the confined structures (see, e.g. Kristensen et al., Natl Acad Sci USA 102, 1779-1784, (2005)). Peroxisomes, as an example, harbor a variety of oxidases with important metabolic and catabolic functions; toxic intermediates, such as hydrogen peroxide ($H_2O_2$) (see, e.g. Wanders et al., Annu Rev Biochem 75, 295-332, (2006); and Schrader et al., Histochem Cell Biol 122, 383-393, (2004)). Interestingly, nature circumvents this dilemma by incorporating catalase (Cat) within the peroxisomes. Catalase is highly active and specific in decomposing $H_2O_2$; rapid elimination of the as-generated $H_2O_2$ prevents its diffusion out from the peroxisomes and damage to other cellular components (see, e.g. Fujiwara et al., J Biol Chem 275, 37271-37277, (2000); and Sheikh et al., P Natl Acad Sci USA 95, 2961-2966, (1998)).

Although multiple-enzyme architectures commonly exist in nature, current enzyme-based applications, including enzyme catalysis and therapeutics, are still limited to the use of single enzyme or their mixtures (see, e.g. Leader et al., Nat Rev Drug Discov 7, 21-39, (2008); Iso et al., J Microencapsul 6, 165-176, (1989); Nouaimi-Bachmann et al., Biotechnol Bioeng 96, 623-630, (2007); and Mateo et al., Enzyme Microb Tech 40, 1451-1463, (2007)). Inorganic and polymeric materials incorporating multiple enzymes have been extensively studied; however, the enzymes were randomly immobilized within these materials in the forms of thin films or large particles (~100 μm in diameter), excluding their therapeutic applications (see, e.g., Srere et al., P Natl Acad Sci USA 70, 2534-2538, (1973); Mansson et al., P Natl Acad Sci. Biol 80, 1487-1491, (1983); Kochschmidt et al., Eur J Biochem 81, 71-78, (1977); and Sheldon et al., Adv Synth Catal 349, 1289-1307, (2007)).

Fusion-protein techniques provide one strategy to construct multiple-enzyme architectures (see, e.g. Riedel et al., Mol Microbiol 28, 767-775, (1998); Shibuya et al., Biosci Biotech Bioch 56, 884-889, (1992); and Mao et al., J Biol Chem 270, 18295-18300, (1995). Ideally, such architectures with designable functions may be achieved by judiciously engineering the genomic inputs transfected to the host cells; nonetheless, this approach often leads to a loss or decreased enzyme specificity and activity (see, e.g. Stempfer et al., Nat Biotechnol 14, 481-484, (1996); and Seo et al., Appl Environ Microb 66, 2484-2490, (2000)). Moreover, finding suitable host cells and designing suitable spacers further place hurdles in the construction of fusion proteins (see, e.g. Bulow et al., Bio-Technol 3, 821-823, (1985)). Recently, post-translational assemblies were used to construct enzyme complexes; however, such an assembling process solely relies on specific bindings between the enzyme components and lacks general applicability (see, e.g., Mingardon et al., Appl Environ Microb 73, 7138-7149, (2007); Fierobe et al., J Biol Chem 276, 21257-21261, (2001); and Fierobe et al., J Biol Chem 277, 49621-49630, (2002)).

SUMMARY

The invention disclosed herein provides robust artificial enzyme nanocomplexes with programmable functions. As discussed in detail below, by using simple wet-chemical approaches novel enzyme nanocomplexes can be created and specifically designed for a broad ranges of functional applications.

The present disclosure provides nanocomplexes containing at least two different enzymes and a polymer network anchored to at least one of the enzymes. Such multiple-enzyme complexes enable the enzymes to carry out their activities cooperatively. In some embodiments, the activities of the enzymes catalyze a cascade reaction. Further, the function of the complexes is programmable through a simple chemical approach. As demonstrated in the experimental examples, these enzyme complexes (termed "Enzyme Nanocomplexes (EN)") exhibit enhanced catalytic efficiencies as well as an increased stability. Simultaneously, these enzyme complexes can be designed to break down specific compounds, for example those that can be toxic in in vivo environments (e.g. hydrogen peroxide).

Thus, in one embodiment, the present disclosure provides a multiple-enzyme nanocomplex comprising at least two different enzymes and a polymeric network which is anchored to at least one of the at least two different enzymes. In one embodiment, the polymeric network is anchored to all of the at least two different enzymes. In one embodiment, the activities of the two different enzymes catalyze a cascade reaction.

In some embodiments, the at least two different enzymes are covalently or non-covalently linked to one another. In one aspect, the covalent linkage is degradable in vivo. In another aspect, the at least two different enzymes are not linked to one another. In one embodiment, the polymeric network comprises a polymer composed of at least one monomeric unit. In another embodiment, the polymeric network comprises a polymer composed of at least two different monomeric units. In some embodiments, the polymeric network further comprises a crosslinker.

Also provided, in one embodiment, is a multiple-enzyme nanocomplex comprising at least two different enzymes and a permeable shell, the shell comprising a polymeric network which is anchored to at least one of the at least two different enzymes. The present disclosure further provides, in another embodiment, a multiple-enzyme nanocomplex consisting essentially of a polymeric network and at least two different enzymes, the polymeric network is covalently anchored to at least one of the at least two different enzymes and provides a permeable shell around the at least two different enzymes.

Yet another embodiment of the invention is multiple-enzyme nanocomplex system that includes elements and architectures (e.g. specific 3-dimensional constellations of elements) designed to facilitate multiple enzymatic reactions. Working embodiments of the systems disclosed herein include a first enzyme that generates hydrogen peroxide in a first enzymatic reaction with a first substrate, a second enzyme that converts the hydrogen peroxide into water in a second enzymatic reaction, and a polymeric network configured to form a shell that encapsulates the first enzyme and the second enzyme. In such system embodiments, the polymeric network exhibits a permeability sufficient to allow the first substrate to diffuse from an external environment outside of the shell to the first enzyme so that the hydrogen peroxide is generated and further exhibits a permeability sufficient to allow the hydrogen peroxide to diffuse away from the first enzyme and to the second enzyme so that the water is generated. In certain embodiments of the invention, the first enzyme is coupled to the second enzyme. In some embodiments of the invention, the polymeric network is coupled to a polypeptide of the first enzyme or a polypeptide of the second polypeptide.

Methods are also provided, in one embodiment, for producing a multiple-enzyme nanocomplex disclosed herein by, for example: (a) linking the at least two different enzymes to one another; (b) acrylating the linked enzymes produced by (a); and (c) in situ polymerizing the acrylated enzymes produced by (b) using at least one monomeric unit and optionally a crosslinker. In one aspect, the methods further comprise (d) removing the linkage. In certain methodological embodiments of the invention, the linking comprises (i) conjugating a ligand specific to each enzyme to single nucleic acid; (ii) effecting the ligand conjugated to the nucleic acid to bind to the enzyme; and (iii) providing a condition under which nucleic acid hybridization occurs. In one aspect, the linking comprises conjugating the enzymes to single nucleic acid strands that are hybridizable to each other. In another aspect, the linking in (a) comprises the use of a linker.

BRIEF DESCRIPTION OF THE DRAWINGS

Throughout the drawings and the application, enzyme nanocomplexes (ENs) are denoted as n(Enzymes), where Enzymes within the parentheses refer to the enzymes within the core of the nanocomplexes. For instance, n(Cat) refers to an EN containing catalase (Cat). n(HRP-GOx-Inv), in the same vein, refers to an EN containing horseradish peroxidase (HRP), glucose oxidase (GOx) and invertase (Inv).

Other abbreviations includes: AOx: alcohol oxidase; ssDNA: single strand DNA; EDAC: 1-ethyl-3-(3-dimethylaminopropyl) carbodiimide; NAS: N-hydroxysuccinimide ester; DLS: dynamic light scattering; TEM: transmission electron microscopy.

DETAILED DESCRIPTION

Figure 1:
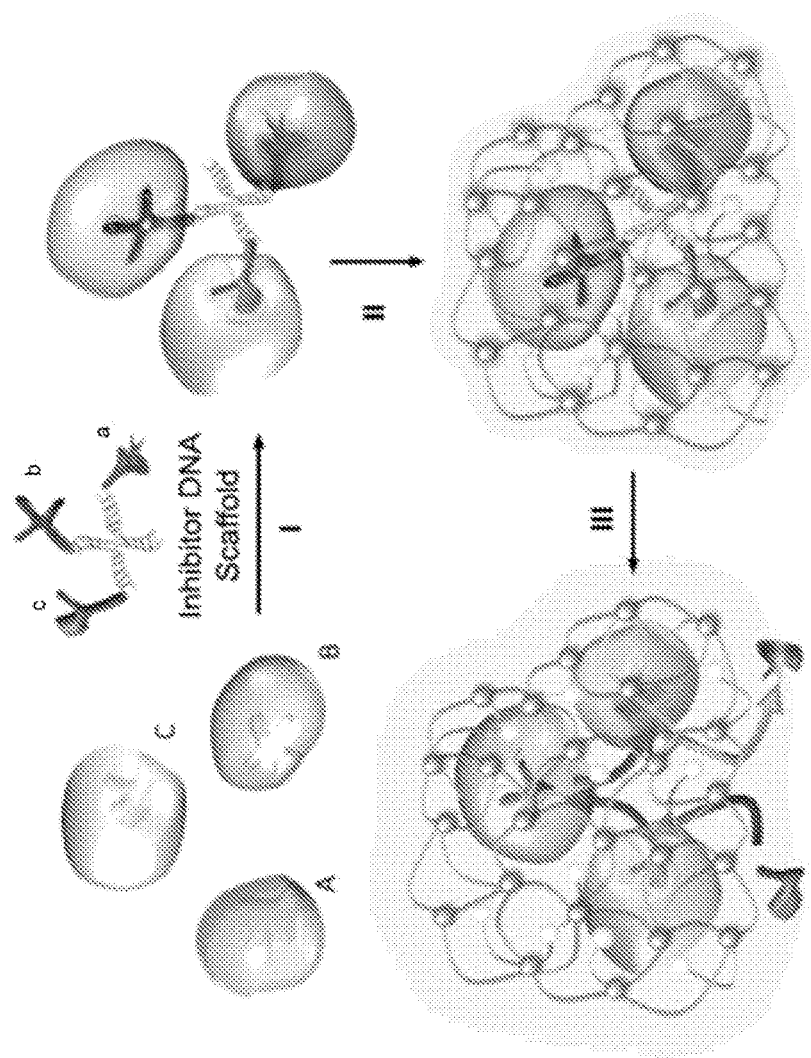
FIG. 1 is a schematic illustration of synthesis of a triple-enzyme nanocomplex by DNA-directed assembly and nano-encapsulation. I. Spontaneous assembly of (A) invertase (Inv), (B) glucose oxidase (GOx), and (C) horseradish peroxidase (HRP) with an inhibitor-DNA scaffold containing their respective competitive inhibitors: (a) lactobionic acid, (b) glucosamine, and (c) 4-dimethylaminoantipyrine leading to the formation of a triple-enzyme architecture. II. Stabilization of the triple-enzyme architecture occurs by in-situ growth of a thin network polymer which spatially constricts the enzyme nanocomplex; III. Removal of the DNA scaffold leading to the formation of triple-enzyme nanocomplexes with significantly enhanced stability and close-proximity definition. Such a close-proximity architecture enables active transport of their reaction intermediates among the enzymes, leading to significantly enhanced reaction efficiency.

Before the compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

When a numerical designation is preceded by the term "about", it varies by (+) or (−) 10%, 5% or 1%. When "about" is used before an amount, for example, in mg, it indicates that the weight value may vary (+) or (−) 10%, 5% or 1%.

Definitions

In accordance with the present invention and as used herein, the following terms are defined with the following meanings, unless explicitly stated otherwise.

As used in the specification and claims, the singular form "a", "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

As used herein, the term "nanocomplex" refers to a structure sized between one and a few hundred nanometers in at least one dimension. In some embodiments, it refers to a structure containing a finite number of chemical and/or biological molecules optionally connected with polymers.

As used herein, the term "spatially constrained" refers to the location of a particle, such as an enzyme, being relatively limited in space relative to another object, such as a polymer network. In some embodiments, it refers to two or more particles having substantially fixed locations relative to each other.

As used herein, the term "polymeric network" or alternatively "polymeric mesh" refers to one or more polymers interconnected within and/or between each other to form a net or mesh. In some embodiments, the polymeric network is anchored to one or more particles at one or more locations.

As used herein, the term "cooperatively" refers to two or more enzymes functioning in a concerted manner. One example is that the two or more enzymes form an enzyme complex, or alternatively react with the same substrate simultaneously, to carry out their activities. In another embodiment, one of the enzymes reacts with the substrate first, producing a product, which in turn, is a substrate that reacts with another of the enzymes.

As used herein, the term "metabolic pathway" refers to a series of chemical reactions occurring within a cell. In each pathway, a principal chemical is modified by a series of chemical reactions. Lists of metabolic pathways are available publicly from, e.g., the KEGG Pathway Database (available at www.genome.jp/kegg/pathway.html). Also, as used herein the term "metabolites" refers to intermediates and products of metabolism. The term metabolite is usually restricted to small molecules. Metabolites have various functions, including fuel, structure, signaling, stimulatory and inhibitory effects on enzymes, catalytic activity of their own (usually as a cofactor to an enzyme), defense, and interactions with other organisms (e.g. pigments, odorants, and pheromones). A primary metabolite is directly involved in normal growth, development, and reproduction. Alcohol is an example of a primary metabolite produced in large-scale by industrial microbiology. A secondary metabolite is not directly involved in those processes, but usually has an important ecological function. Examples include antibiotics and pigments such as resins and terpenes, etc. Some antibiotics use primary metabolites as precursors, such as actinomycin which is created from the primary metabolite, tryptophan.

Multiple-Enzyme Nanocomplexes

The present disclosure provides multiple-enzyme nanocomplexes, or enzyme nanocomplexes (ENs), that show enhanced catalytic efficiency and increased stability, and at the same time can reduce, when necessary, the release of intermediates that may be toxic to the environment.

The invention disclosed herein has a number of embodiments. Embodiments of the present invention include nanocomplexes containing at least two different enzymes, and a polymer network. Typically, the polymer network is anchored to at least one of the enzymes. Such multiple-enzyme complexes enable the enzymes to carry out their activities cooperatively. As demonstrated in the experimental examples, these enzyme complexes (termed "Enzyme Nanocomplexes (EN)") exhibit enhanced catalytic efficiencies as well as an increased stability. Simultaneously, these enzyme complexes can be designed to break down specific compounds, for example those that can be toxic in in vivo environments (e.g. hydrogen peroxide). In some embodiments, the activities of the enzymes catalyze a cascade reaction. Further, the function of the complexes is programmable through a simple chemical approach.

Embodiments of the invention include a multiple-enzyme nanocomplex comprising at least two different enzymes and a polymeric network. Typically, the polymer network is anchored to at least one of the at least two different enzymes. In one embodiment, the polymeric network is anchored to all of the at least two different enzymes. In other embodiments, different enzymes in the nanocomplex are anchored together, for example via complementary polynucleotide strands.

In illustrative embodiments of the invention, the at least two different enzymes are covalently or non-covalently linked to one another. In one aspect, the covalent linkage is degradable in vivo. In another aspect, the at least two different enzymes are not linked to one another. In one embodiment, the polymeric network comprises a polymer composed of at least one monomeric unit. In another embodiment, the polymeric network comprises a polymer composed of at least two different monomeric units. In some embodiments, the polymeric network further comprises a crosslinker.

Embodiments of the invention include a multiple-enzyme nanocomplex comprising at least two different enzymes and a permeable shell, the shell comprising a polymeric network which is anchored to at least one of the at least two different enzymes. The present disclosure further provides, in another embodiment, a multiple-enzyme nanocomplex consisting essentially of a polymeric network and at least two different enzymes, the polymeric network is covalently anchored to at least one of the at least two different enzymes and provides a permeable shell around the at least two different enzymes.

Related embodiments of the invention include a multiple-enzyme nanocomplex comprising at least two different enzymes and a polymeric network which is anchored to at least one of said at least two different enzymes, wherein said polymer network comprises a crosslinker. In certain embodiments, the crosslinker is a degradable crosslinker. Optionally, the crosslinker is a degradable crosslinker comprising a N,N'-methylenebis(acrylamide), a 1,4-bis(acryloyl)piperazine, an ethylene glycol diacrylate, a N,N'-(1,2-dihydroxyethylene)bisacrylamide, or a poly(ethylene glycol)diacrylate. In certain embodiments, the crosslinker is a non-degradable crosslinker. Optionally, the crosslinker is a non-degradable crosslinker comprising a N,N'-bis(acryloyl) cystamine, a glycerol dimethacrylate, a bis[2-(methacryloyloxy)ethyl]phosphate or a bisacryloylated polypeptide.

Yet another embodiment of the invention is multiple-enzyme nanocomplex system that includes elements and architectures (e.g. specific 3-dimensional constellations of elements) combined together in a manner designed to facilitate certain enzymatic reactions. Exemplary embodiments include multiple-enzyme nanocomplex system comprising a first enzyme that generates a first product in a first enzymatic reaction with a first substrate, a second enzyme that reacts with the first product in a second enzymatic reaction, and a polymeric network configured to form a shell that encapsulates the first enzyme and the second enzyme. Typically in such systems, the polymeric network exhibits a permeability sufficient to allow the first substrate to diffuse from an external environment outside of the shell to the first enzyme so that the first product is generated. In such systems the polymeric network can also exhibit a permeability sufficient to allow the first product to diffuse away from the first enzyme and to the second enzyme so that the second enzymatic reaction occurs. In common system embodiments, the first enzyme is coupled to the second enzyme, or the polymeric network is coupled to a polypeptide of the first enzyme or a polypeptide of the second enzyme.

Illustrative working embodiments of the systems disclosed herein include a first enzyme that generates hydrogen peroxide in a first enzymatic reaction with a first substrate, a second enzyme that converts the hydrogen peroxide into water ($H_2O$) and/or oxygen ($O_2$) in a second enzymatic reaction, and a polymeric network configured to form a shell that encapsulates the first enzyme and the second enzyme. In such system embodiments the polymeric network exhibits a permeability sufficient to allow the first substrate (e.g. ethanol) to diffuse from an external environment outside of the shell to the first enzyme so that the hydrogen peroxide is generated. The polymer network in this embodiment is designed to further exhibit a permeability sufficient to allow the hydrogen peroxide to diffuse away from the first enzyme and to the second enzyme so that the water is generated. In certain embodiments of the invention, the first enzyme is coupled to the second enzyme. In some embodiments of the invention, the polymeric network is coupled to a polypeptide of the first enzyme or a polypeptide of the second enzyme.

In typical systems of the invention, the polymeric network encapsulates the first enzyme and the second enzyme in a manner sufficient to inhibit degradation of the first enzyme or the second enzyme when the multiple-enzyme nanocomplex is disposed in an in vivo environment. In common embodiments, the first enzyme and the second enzyme are coupled together, optionally for example, through the use of a chemical linker or tether. In certain working embodiments of the invention that are disclosed herein, the first enzyme and the second enzyme are coupled together by strands of complementary polynucleotides.

A wide variety of enzymes can be used in various embodiments of the invention. In one of the working embodiments disclosed herein, the first enzyme is an alcohol oxidase; and the second enzyme is a catalase. In another of the working embodiments disclosed herein, the first enzyme is a glucose oxidase; and the second enzyme is a horseradish peroxidase.

Certain embodiments of the invention include a third enzyme encapsulated within the polymeric network (e.g. an aldehyde dehydrogenase, an alcohol dehydrogenase or the like).

As noted above, a wide variety of enzymes can be used in various embodiments of the invention. Certain embodiments of the invention can comprise a catalase that can catalyze the decomposition of hydrogen peroxide to water and/or oxygen. Catalases can also catalyze the oxidation, by hydrogen peroxide, of various metabolites and toxins, including formaldehyde, formic acid, phenols, acetaldehyde and alcohols. Catalases typically do so according to the following reaction:

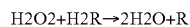

$$H2O2+H2R \rightarrow 2H2O+R$$

A number of catalase polypeptides that can be used in embodiments of the invention are well known in the art; for example, catalase polypeptides derived from human erythrocytes (e.g. SIGMA-ALDRICH product number C3556), bovine liver (e.g. SIGMA-ALDRICH product number C1345), bison liver (e.g. SIGMA-ALDRICH product number C9447), *Aspergillus niger* (e.g. SIGMA-ALDRICH product number C3515), *Corynebacterium glutamicum* (e.g. SIGMA-ALDRICH product number 02071), *Micrococcus lysodeikticus* (e.g. SIGMA-ALDRICH product number 60634) etc.

Certain embodiments of the invention can comprise a peroxidase. Peroxidases (EC number 1.11.1.x) are enzymes that typically catalyze a reaction of the form:

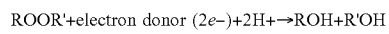

$$ROOR'+\text{electron donor } (2e-)+2H+ \rightarrow ROH+R'OH$$

For many of these enzymes the optimal substrate is hydrogen peroxide, but others are more active with organic hydroperoxides such as lipid peroxides. Peroxidases can contain a heme cofactor in their active sites, or alternately redox-active cysteine or selenocysteine residues. A number of peroxidase polypeptides that can be used in embodiments of the invention are known in the art; for example, peroxidase polypeptides derived from horseradish, (e.g. SIGMA-ALDRICH product number P8375), glutathione peroxidase derived from human erythrocytes, (e.g. SIGMA-ALDRICH product number G4013) etc.

Certain embodiments of the invention can comprise an alcohol oxidase. Typical alcohol oxidases (EC 1.1.3.13) catalyze the chemical reaction:

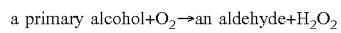

$$\text{a primary alcohol}+O_2 \rightarrow \text{an aldehyde}+H_2O_2$$

In this illustration, the two substrates of this enzyme are primary alcohol and $O_2$, and its two products are aldehyde and $H_2O_2$. A number of alcohol oxidase polypeptides that can be used in embodiments of the invention are known in the art; for example those derived from yeast (e.g. SIGMA-ALDRICH product number A6941), *Hansenula polymorpha* (e.g. SIGMA-ALDRICH Catalog Number A0438), *Pichea pastoris* (e.g. MP BIOMEDICALS Catalog Number: 190155) etc.

Certain embodiments of the invention can comprise an aldehyde oxidase. Typical aldehyde oxidase enzymes generate carboxylic acids from aldehydes, for example by catalyzing the conversion of an aldehyde in the presence of oxygen and water to an acid and hydrogen peroxide:

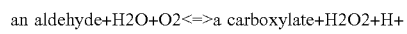

$$\text{an aldehyde}+H2O+O2 \iff \text{a carboxylate}+H2O2+H+$$

A number of aldehyde oxidase polypeptides that can be used in embodiments of the invention are known in the art; for example human recombinant polypeptides (e.g. CYPEX product number CYP150, LABOME product number TP319221) etc.

Certain embodiments of the invention can comprise a glucose oxidase. Glucose oxidases are oxido-reductases that catalyze the oxidation of glucose to hydrogen peroxide and D-glucono-δ-lactone. A number of glucose oxidase polypeptides that can be used in embodiments of the invention are known in the art; for example those derived from *Aspergillus niger* (e.g. SIGMA-ALDRICH product number G7141), *Dactylium dendroides* (e.g. SIGMA-ALDRICH product number G7907) etc.

Certain embodiments of the invention can comprise an invertase, for example to catalyze the hydrolysis of sucrose. A number of invertase polypeptides that can be used in embodiments of the invention are known in the art; for example, invertase polypeptides purified from organisms such as yeast (e.g. SIGMA-ALDRICH product number 14504) etc.

Certain embodiments of the invention can comprise a urate oxidase. Urate oxidase, or uricase (EC 1.7.3.3), is a peroxisomal liver enzyme that catalyses the enzymatic oxidation of uric acid into the more water-soluble allantoin. Urate oxidase is an endogenous enzyme found in most mammals but not in humans. Urate oxidase is used in humans for the control of increased serum uric acid in patients with acute tumor lysis syndrome after receiving chemotherapy. Rasburicase (SR 29142), a recombinant urate oxidase expressed in *Saccharomyces cerevisiae*, has been demonstrated to be superior to allopurinol in the control of uric acid in a randomized trial of pediatric and adult patients at risk of acute tumour lysis syndrome. In addition, urate oxidase is used in the treatment of gout. A number of urate oxidase polypeptides that can be used in embodiments of the invention are known in the art; for example recombinant forms (e.g. Rasburicase) as well as forms derived from *Aspergillus flavus* (e.g. PROSPEC BIO product number ENZ-312), yeast (e.g. WORTHINGTON BIOCHEMICAL product no. LS003857) etc.

Certain embodiments of the invention can comprise an aldehyde dehydrogenase such as a acetaldehyde dehydrogenase. Acetaldehyde dehydrogenases (EC 1.2.1.10) are dehydrogenase enzymes which catalyze the conversion of acetaldehyde into acetic acid. The oxidation of acetaldehyde to acetate can be summarized as follows:

In humans, there are a number of genes which encode this enzymatic activity including, ALDH1A1, ALDH2, and ALDH1B1 (also known as ALDH5). These enzymes are members of the larger class of aldehyde dehydrogenases. The CAS number for this type of the enzyme is [9028-91-5]. Certain embodiments of the invention can comprise an aldehyde dehydrogenase, for example to catalyze the oxidation (dehydrogenation) of aldehydes. A number of aldehyde dehydrogenase polypeptides that can be used in embodiments of the invention are known in the art; for example, recombinant human aldehyde dehydrogenase polypeptides (e.g. R & D SYSTEMS product number 5869-DH), as well as aldehyde dehydrogenase polypeptides purified from organisms such as yeast (e.g. SIGMA-ALDRICH product number A6338) etc.

Certain embodiments of the invention can comprise an alcohol dehydrogenase, for example to facilitate the interconversion between alcohols and aldehydes or ketones with the reduction of nicotinamide adenine dinucleotide (NAD+ to NADH). A number of alcohol dehydrogenase polypeptides that can be used in embodiments of the invention are known in the art; for example, purified human alcohol dehydrogenase polypeptides (e.g. ARP AMERICAN RESEARCH PRODUCTS INC. product number 01-1746), recombinant human alcohol dehydrogenase polypeptides (e.g. MYBIOSOURCE Catalog # MBS203604), as well as alcohol dehydrogenase polypeptides derived from Equine liver (e.g. SIGMA-ALDRICH product number 05646), *Saccharomyces cerevisiae* (e.g. SIGMA-ALDRICH product number A7011), *Parvibaculum lavamentivorans* (e.g. SIGMA-ALDRICH product number 75449) etc.

Certain embodiments of the invention can comprise a formate dehydrogenase, for example to catalyze the oxidation of formate to bicarbonate. A number of formate dehydrogenase polypeptides that can be used in embodiments of the invention are known in the art; for example, recombinant polypeptides (e.g. SIGMA-ALDRICH product number 75274) as well as formate dehydrogenase polypeptides purified from organisms such as yeast (e.g. SIGMA-ALDRICH product number F8649) etc.

Certain embodiments of the invention can comprise a glucose-6-phosphatase, for example to hydrolyze glucose-6-phosphate in a manner that generates a phosphate group and free glucose. A number of glucose-6-phosphatase polypeptides that can be used in embodiments of the invention are known in the art; for example, glucose-6-phosphatase polypeptides purified from rabbit liver (e.g. SIGMA-ALDRICH product number G5758) etc.

Certain embodiments of the invention can comprise a glucosidase, for example, one useful for the degradation of glycogen to glucose (e.g. an acid maltase). A number of α-glucosidase polypeptides that can be used in embodiments of the invention are known in the art; for example, recombinant human α-glucosidase α (e.g. NOVUS BIOLOGICALS product No. H00023193-P01) as well as -glucosidase polypeptides purified from organisms such as yeast (e.g. SIGMA-ALDRICH product number G0660) etc.

Certain embodiments of the invention can comprise a glycogen branching enzyme, for example one useful in converting glucose to glycogen. A number of glycogen branching enzyme polypeptides that can be used in embodiments of the invention are known in the art; for example, recombinant human α-glucosidase α (e.g. NOVUS BIOLOGICALS product No. H0002632-P01) as well as -glucosidase polypeptides purified from organisms such as E. Coli (e.g. PROZOMIX product number PRO-E0406) etc.

Certain embodiments of the invention can comprise a coenzyme A dehydrogenase, for example, one useful to catalyze a step in each cycle of fatty acid β-oxidation. A number of coenzyme A dehydrogenase polypeptides that can be used in embodiments of the invention are known in the art; for example, recombinant human coenzyme A dehydrogenase polypeptides (e.g. MYBIOSOURCE Catalog # MBS142535) etc.

Certain embodiments of the invention can comprise a organic cation/carnitine transporter, for example, one useful as an organic cation transporter and/or as a sodium-dependent high affinity carnitine transporter. A number of OCTN2 polypeptides that can be used in embodiments of the invention are known in the art; for example, recombinant human OCTN2 (e.g. NOVUS BIOLOGICALS SLC22A5 Recombinant Protein product no. H00006584-P01) etc.

In addition to the illustrative enzymes disclosed above, any one of the large number of polypeptides encoded by known genes (e.g. those disclosed herein and listed in GENBANK, UniProtKB/Swiss-Prot and the like) can be readily made by commercially available recombinant protein services such as those provided by GENSCRIPT.

In some embodiments of the invention, a composition or system embodiment of the invention is disposed in a kit comprising a container and instructions for using the multiple-enzyme nanocomplex system. Optionally in such kits, the system is combined with one or more filling agents, binding agents or buffering agents adapted for use in an orally administered formulation. In some embodiments of the invention, the system is combined with one or more filling agents, binding agents or buffering agents adapted for use in an parenterally administered formulation.

Embodiments of the invention include articles of manufacture and/or kits, for example those containing materials useful in breaking down certain compounds in vivo such as hydrogen peroxide. Optionally, the articles of manufacture and/or kits can contain materials useful in treating a pathological condition such as acute alcohol poisoning. In typical embodiments of the invention, the kit comprises at least one container, typically with a label Suitable containers include, for example, blister packs, bottles, vials, and test tubes. The containers may be formed from a variety of materials such as metal (e.g. a metal foil), glass or plastic. In some embodiments of the invention, the one or more containers holds one or more compositions having an active agent which is effective in imaging techniques. In certain embodiments of the invention, the one or more containers holds one or more compositions having an active agent which is effective in treating a pathological condition such as acute alcohol poisoning. Typically, the label on the one or more containers indicates that the one or more compositions is used for in treating a pathological condition. Such labels may also indicate directions for either in vivo or in vitro use, such as those described herein. The kits of the invention can also comprise the one or more containers described above and a further container comprising a buffer. Kits may further include other materials desirable from a commercial and user standpoint, including other buffers, diluents, filters, needles, syringes, and package inserts with instructions for use.

In certain embodiments of the invention, a composition or enzyme nanocomplex system disclosed herein is formulated as an agent designed to ameliorate or treat a pathological condition such as alcohol toxicity. For example, in certain embodiments of the invention, a composition or enzyme nanocomplex system disclosed herein is formulated as an agent designed to prevent a pathological condition such as alcohol toxicity. The agent may be administered via a conventional route normally used to administer a medicament including, but not limited to, oral, parenteral (including subcutaneous, intradermal, intramuscular, intravenous, intraarticular, and intramedullary), intraperitoneal, transmucosal (including nasal), transdermal, rectal and topical (including dermal, buccal, sublingual and intraocular) routes. Intravenous delivery may take place via a bolus injection or via infusion; infusion may be done over a period ranging from less than a minute to several hours to continuously. In certain embodiments, a course of treatment will involve administration by a combination of routes.

The agent may be administered via a combination of intravenous and oral routes for the treatment of pain or another disorder. In one embodiment, a "loading" dose may be administered IV in order to bring the concentration of drug to the desired therapeutic level, followed by one or more maintenance doses via the oral route to keep it there. The agent may be administered as a pharmaceutical composition in a variety of forms including, but not limited to, liquid, powder, suspensions, tablets, pills, capsules, sprays and aerosols. The pharmaceutical compositions may include various pharmaceutically acceptable additives including, but not limited to, carriers, excipients, binders, stabilizers, antimicrobial agents, antioxidants, diluents and/or supports. Examples of suitable excipients and carriers are described, for example, in "Remington's Pharmaceutical Sciences," Mack Pub. Co.; 17th edition New Jersey (2011). In some embodiments, the agent may be administered via an IV infusion in an aqueous sugar solution. The agent may also be associated with another substance that facilitates agent delivery. For example, the agent may be associated into liposomes. The liposomes, in turn, may be conjugated with targeting substance(s), such as IgGFc receptors.

Formulations of the compounds disclosed herein suitable for oral administration may be presented as discrete units such as capsules, cachets or tablets each containing a pre-determined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Examples of fillers, or diluents, include, without limitation, lactose, mannitol, xylitol, dextrose, sucrose, sorbitol, compressible sugar, microcrystalline cellulose (MCC), powdered cellulose, cornstarch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers such as polyethylene oxide, and hydroxypropyl methyl cellulose. Fillers may have complexed solvent molecules, such as in the case where the lactose used is lactose monohydrate. Disintegrants that can be adapted for use with embodiments of the compositions herein include, without limitation, sodium starch glycolate, sodium carboxymethyl cellulose, calcium carboxymethyl cellulose, croscarmellose sodium, povidone, crospovidone (polyvinylpolypyrrolidone), methyl cellulose, microcrystalline cellulose, powdered cellulose, low-substituted hydroxy propyl cellulose, starch, pregelatinized starch, and sodium alginate. Tablet binders to be used in the compositions herein include, without limitation, acacia, alginic acid, carbomer, carboxymethyl cellulose sodium, dextrin, ethylcellulose, gelatin, guar gum, hydrogenated vegetable oil, hydroxyethylcellulose, hydroxypropyl cellulose, hydroxypropylmethyl cellulose, copolyvidone, methyl cellulose, liquid glucose, maltodextrin, polymethacrylates, povidone, pregelatinized starch, sodium alginate, starch, sucrose, tragacanth, and zein.

The addition of pH modifiers such as acids, bases, or buffers may also be beneficial, retarding or enhancing the rate of dissolution of the composition, or, alternatively, helping to improve the chemical stability of the composition. In addition, the formulations provided herein may include other agents conventional in the art having regard to the type of formulation in question. Proper formulation is dependent upon the route of administration chosen. Any of the well-known techniques, carriers, and excipients may be used as suitable and as understood in the art; e.g., Remington, supra. The pharmaceutical compositions may be manufactured in a manner that is itself known, e.g., by means of conventional mixing, dissolving, granulating, dragee-making, levigating, emulsifying, encapsulating, entrapping or compression processes.

As shown by the working embodiments of the invention, a close-proximity architecture endows the ENs with significantly enhanced catalytic efficiency. This was demonstrated by consecutive reactions of sucrose and glucose mediated by invertase (Inv), glucose oxidase (GOx) and horseradish peroxidase (HRP). Glucose directly added in the reaction media or generated from the Inv-mediated hydrolysis of sucrose is oxidized via the GOx-mediated reaction, leading to the production of $H_2O_2$. The produced $H_2O_2$ then further oxidizes o-dianisidine via the HRP-mediated reaction. The architecture of this invention is unique not only in that the multiple enzymes within the nanocomplexes are able to be spatially confined with each other but that such spatial confinement acts cooperatively (synergistically) rather than antagonistically.

As shown in Example 1, the turnover rates (o-dianisidine oxidation rates) of n(HRP-GOx) and n(HRP-GOx-Inv), compared to those of their native enzyme mixtures with the same enzyme contents, were 5 and 15 folds higher, respectively, confirming an enhanced catalytic efficiency. As used throughout the disclosure, enzyme nanocomplexes (ENs) are denoted as n(Enzymes), where Enzymes within the parentheses refer to the enzymes within the core of the nanocomplexes. For instance, n(Cat) refers to an EN containing catalase (Cat) and n(HRP-GOx-Inv) refers to an EN containing horseradish peroxidase (HRP), glucose oxidase (GOx) and invertase (Inv).

Further, in the presence of 35 wt-% polyethylene glycol (PEG, Mw~3000), a condition to simulate the viscous environment within the cells or blood stream, n(HRP-GOx) achieved a 34 fold increase, as compared to the corresponding enzyme mixtures, in turnover rates. Similarly, n(HRP-GOx-Inv) showed up to 24-fold enhancement in relative turnover rates in PEG solutions.

Figure 2:
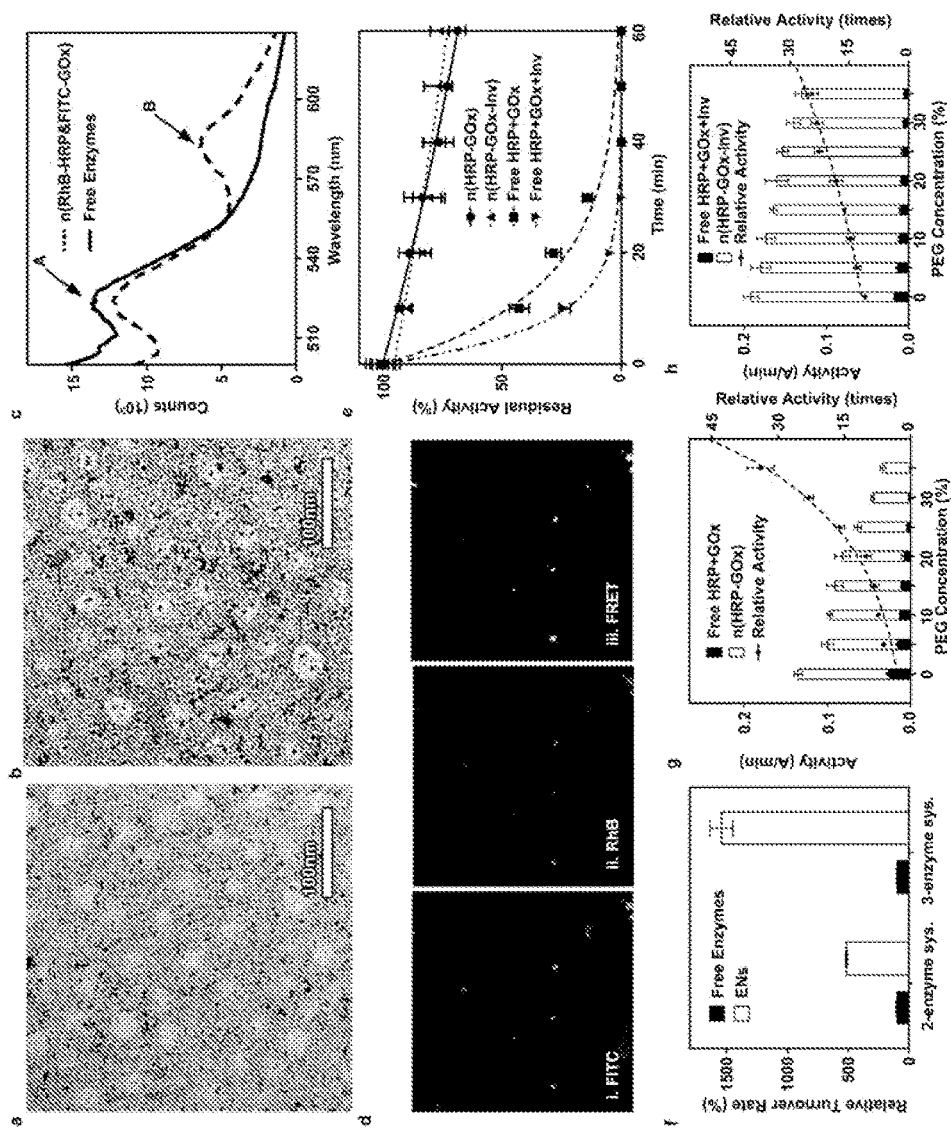
FIG. 2 includes images and charts to demonstrate the structure and enhanced activity and stability of enzyme nanocomplexes. (a) Transmission electron microscopic (TEM) image of n(HRP-GOx) with uniform size. (b) TEM image of n(HRP-GOx) prepared from HRP and GOx that were respectively labeled with a single gold nanoparticle, confirming a dual-enzyme nanocomplex architecture. (c) Fluorescence spectra of n(HRP-GOx) and a mixture of n(HRP) and n(GOx) with the same protein content. The GOx and HRP were pre-labeled with FITC and RhB, respectively. The spectrum was recorded using Ex=450 nm. (d) Confocal microscopic images of (i) n(FITC-labeled GOx) (Ex=488 nm, Em=510~530 nm), (ii) n(RhB-labeled HRP) (Ex=532 nm, Em=570~600 nm), and n(HRP-GOx) synthesized with the FITC-labeled GOx and RhB-labeled HRP (Ex=488 nm, Em=570~600 nm). (e) Comparison of enzyme stabilities of n(HRP-GOx), n(HRP-GOx-Inv) and their native-enzyme-mixture counterparts at 65° C. (f) Comparison of the turnover rates of n(HRP-GOx) and n(HRP-GOx-Inv) (ENs) with their native-enzyme-mixture counterparts (Free Enzymes), denoted as 2-enzyme system and 3-enzyme systems, respectively. The turnover rates were normalized vs. those of the corresponding native enzyme mixtures. (g) Activity comparison of n(HRP-GOx) and a mixture of native HRP and GOx with same enzyme content with increasing poly(ethylene glycol) (PEG) concentration in phosphate buffer (50 mM, pH=7.0). (h) Activity comparison of n(HRP-GOx-Inv) and a mixture of native HRP, GOx, and Inv with same enzyme content with increasing PEG concentration. The relative activities were normalized by the activities of the free-enzyme mixtures at the same enzyme content and PEG concentration.

Moreover, significantly enhanced stability of the enzymes in the ENs have also been observed. As shown in FIG. 2e, n(HRP-GOx) and n(HRP-GOx-Inv) retained 70% and 75% of the residual enzyme activities, respectively, after incubation at 65° C. for 60 minutes. Under the same condition, the free enzymes lose more than 98% of their activities.

Still further, the ENs release less intermediates than the free enzyme mixtures. In the case of GOx and Cat, the intermediates include $H_2O_2$, which is toxic and may cause damages to organs and tissues. The in vitro data in Example 1 show that GOx alone, when incubated with cells, led to a loss of 90% cell viability owing to the $H_2O_2$ generated from GOx-mediated glucose oxidation. When co-incubated with Cat, the loss went down to 58%. In the presence of n(GOx-Cat), however, such loss went down, dramatically, to 9%. Similar results, measured by skin damages, were also observed in vivo.

Also shown in Example 1 is an enzyme nanocomplex, n(AOx-Cat), containing alcohol oxidase (AOx) and catalase (Cat), and the nanocomplex's potential as an antidote for alcohol. Both in vitro and in vivo experiments demonstrated the significant effect of n(AOx-Cat) in metabolizing alcohol and reducing alcohol-induced liver damages, while minimizing the release of the toxic byproduct, $H_2O_2$. Therefore, the experimental data clearly demonstrate that the enzyme nanocomplexes (ENs) of the present disclosure achieve enhanced catalytic efficiency and increased stability, and at the same time can, when necessary, reduce the release of intermediates that may be toxic, such as $H_2O_2$, to the environment. Thus, one embodiment of the present disclosure provides a nanocomplex comprising two or more enzymes including a first enzyme and a second enzyme and a polymeric network anchored to at least one, or alternatively at least two, or three, or four, or five, or all of the enzymes, wherein the enzymes are spatially constrained by the polymeric network and each enzyme cooperatively reacts with a substrate.

Cooperatively reacting with a substrate, in one embodiment, intends to mean that the enzymes, directly or indirectly, react with the substrate in a concerted manner. In one aspect, the enzymes react with the substrate(s) sequentially. In this respect, the first enzyme may react with a substrate first, converting it into one or more products, such as integrating a substrate with another molecule and degrading it into more than one molecules. The second enzyme then reacts with one or more of the products. In other words, in one embodiment, the product of the first enzyme is a substrate for the second enzyme.

Alternatively, the first and second enzyme can react with the substrate simultaneously. It is well known in the art that enzymes can form complexes and carry out their functions through the complexes. In some instances, the enzymes can still function as a group without forming a physical complex, such as enzymes and their co-factors. Another example is that many enzymes interact with a nucleic acid, such as DNA and RNA, simultaneously, to effect replication, transcription or translation, without having direct physical or functional relationship with each other. All these combinations of enzymes are contemplated for the purpose of this disclosure.

In any of the above disclosure, the nanocomplex further includes a third enzyme, a fourth enzyme, and/or a fifth enzyme and so forth. Each of the additional enzyme can carry out a serial reaction with another enzyme in the nanocomplex, or concurrently function with another enzyme.

In some embodiments, two or more of the enzymes in the nanocomplex belong to a metabolic pathway. Metabolic pathways are known in the art and further described herein. Non-limiting examples of metabolic pathways include glycolysis/gluconeogenesis pathway, citrate cycle (tca cycle) pathway, pentose phosphate pathway, pentose and glucuronate interconversions pathway, fructose and mannose metabolism pathway, galactose metabolism pathway, ascorbate and aldarate metabolism pathway, starch and sucrose metabolism pathway, amino sugar and nucleotide sugar metabolism pathway, pyruvate metabolism pathway, glyoxylate and dicarboxylate metabolism pathway, propanoate metabolism pathway, butanoate metabolism pathway, c5-branched dibasic acid metabolism pathway, inositol phosphate metabolism pathway, oxidative phosphorylation pathway, photosynthesis pathway, photosynthesis—antenna proteins pathway, carbon fixation in photosynthetic organisms pathway, carbon fixation pathways in prokaryotes pathway, methane metabolism pathway, nitrogen metabolism pathway, sulfur metabolism pathway, fatty acid biosynthesis pathway, fatty acid elongation pathway, fatty acid metabolism pathway, synthesis and degradation of ketone bodies pathway, cutin, suberine and wax biosynthesis new! pathway, steroid biosynthesis pathway, primary bile acid biosynthesis pathway, secondary bile acid biosynthesis pathway, steroid hormone biosynthesis pathway, glycerolipid metabolism pathway, glycerophospholipid metabolism pathway, ether lipid metabolism pathway, sphingolipid metabolism pathway, arachidonic acid metabolism pathway, linoleic acid metabolism pathway, alpha-linolenic acid metabolism pathway, and biosynthesis of unsaturated fatty acids pathway.

Further non-limiting examples of metabolic pathways include purine metabolism pathway, pyrimidine metabolism pathway, alanine, aspartate and glutamate metabolism pathway, glycine, serine and threonine metabolism pathway, cysteine and methionine metabolism pathway, valine, leucine and isoleucine degradation pathway, valine, leucine and isoleucine biosynthesis pathway, lysine biosynthesis pathway, lysine degradation pathway, arginine and proline metabolism pathway, histidine metabolism pathway, tyrosine metabolism pathway, phenylalanine metabolism pathway, tryptophan metabolism pathway, phenylalanine, tyrosine and tryptophan biosynthesis pathway, beta-alanine metabolism pathway, taurine and hypotaurine metabolism pathway, phosphonate and phosphinate metabolism pathway, selenocompound metabolism pathway, cyanoamino acid metabolism pathway, D-glutamine and d-glutamate metabolism pathway, D-arginine and d-ornithine metabolism pathway, D-alanine metabolism pathway, and glutathione metabolism pathway.

Further non-limiting examples of metabolic pathways include n-glycan biosynthesis pathway, various types of n-glycan biosynthesis pathway, mucin type o-glycan biosynthesis pathway, other types of o-glycan biosynthesis pathway, glycosaminoglycan biosynthesis—chondroitin sulfate pathway, glycosaminoglycan biosynthesis—heparan sulfate pathway, glycosaminoglycan biosynthesis—keratan sulfate pathway, glycosaminoglycan degradation pathway, glycosylphosphatidylinositol(GPI)-anchor biosynthesis pathway, glycosphingolipid biosynthesis—lacto and neolacto series pathway, glycosphingolipid biosynthesis—globo series pathway, glycosphingolipid biosynthesis—ganglio series pathway, lipopolysaccharide biosynthesis pathway, peptidoglycan biosynthesis pathway, other glycan degradation pathway, thiamine metabolism pathway, riboflavin metabolism pathway, vitamin B6 metabolism pathway, nicotinate and nicotinamide metabolism pathway, pantothenate and CoA biosynthesis pathway, biotin metabolism pathway, lipoic acid metabolism pathway, folate biosynthesis pathway, one carbon pool by folate pathway, retinol metabolism pathway, porphyrin and chlorophyll metabolism pathway, and ubiquinone and other terpenoid-quinone biosynthesis pathway.

Still, further non-limiting examples of metabolic pathways include terpenoid backbone biosynthesis pathway, monoterpenoid biosynthesis pathway, sesquiterpenoid biosynthesis pathway, diterpenoid biosynthesis pathway, carotenoid biosynthesis pathway, brassinosteroid biosynthesis pathway, insect hormone biosynthesis pathway, zeatin biosynthesis pathway, limonene and pinene degradation pathway, geraniol degradation pathway, type I polyketide structures pathway, biosynthesis of 12-, 14- and 16-membered macrolides pathway, biosynthesis of ansamycins pathway, biosynthesis of type II polyketide backbone pathway, biosynthesis of type II polyketide products pathway, tetracycline biosynthesis pathway, polyketide sugar unit biosynthesis pathway, nonribosomal peptide structures pathway, biosynthesis of siderophore group nonribosomal peptides pathway, biosynthesis of vancomycin group antibiotics pathway, phenylpropanoid biosynthesis pathway, stilbenoid, diarylheptanoid and gingerol biosynthesis pathway, flavonoid biosynthesis pathway, flavone and flavonol biosynthesis pathway, anthocyanin biosynthesis pathway, isoflavonoid biosynthesis pathway, indole alkaloid biosynthesis pathway, isoquinoline alkaloid biosynthesis pathway, tropane, piperidine and pyridine alkaloid biosynthesis pathway, acridone alkaloid biosynthesis pathway, caffeine metabolism pathway, betalain biosynthesis pathway, glucosinolate biosynthesis pathway, benzoxazinoid biosynthesis pathway, penicillin and cephalosporin biosynthesis pathway, beta-lactam resistance pathway, streptomycin biosynthesis pathway, butirosin and neomycin biosynthesis pathway, clavulanic acid biosynthesis pathway, puromycin biosynthesis pathway, and novobiocin biosynthesis pathway.

Still, further non-limiting examples of metabolic pathways include benzoate degradation pathway, aminobenzoate degradation pathway, fluorobenzoate degradation pathway, chloroalkane and chloroalkene degradation pathway, chlorocyclohexane and chlorobenzene degradation pathway, toluene degradation pathway, xylene degradation pathway, nitrotoluene degradation pathway, ethylbenzene degradation pathway, styrene degradation pathway, atrazine degradation pathway, caprolactam degradation pathway, DDT degradation pathway, bisphenol degradation pathway, dioxin degradation pathway, naphthalene degradation pathway, polycyclic aromatic hydrocarbon degradation pathway, metabolism of xenobiotics by cytochrome P450 pathway, and drug metabolism—cytochrome P450 pathway.

Metabolic pathways can also include MAPK signaling pathway, MAPK signaling pathway—fly pathway, MAPK signaling pathway—yeast pathway, ErbB signaling pathway, wnt signaling pathway, notch signaling pathway, hedgehog signaling pathway, TGF-beta signaling pathway, VEGF signaling pathway, Jak-STAT signaling pathway, calcium signaling pathway, phosphatidylinositol signaling system pathway, mTOR signaling pathway, plant hormone signal transduction pathway, hematopoietic cell lineage pathway, complement and coagulation cascades pathway, toll-like receptor signaling pathway, NOD-like receptor signaling pathway, RIG-I-like receptor signaling pathway, cytosolic DNA-sensing pathway, natural killer cell mediated cytotoxicity pathway, antigen processing and presentation pathway, T cell receptor signaling pathway, B cell receptor signaling pathway, Fc epsilon RI signaling pathway, Fc gamma R-mediated phagocytosis pathway, leukocyte transendothelial migration pathway, intestinal immune network for IgA production pathway, and chemokine signaling pathway, In a particular embodiment, the two or more enzymes comprise a horseradish peroxidase (HRP) and a glucose oxidase (GOx). In another embodiment, the two or more enzymes comprise a horseradish peroxidase (HRP), a glucose oxidase (GOx) and an invertase (Inv). In another embodiment, the two or more enzymes comprise a glucose oxidase (GOx) and a catalase (Cat). In yet another embodiment, the two or more enzymes comprise an alcohol oxidase (AOx) and a catalase (Cat).

In some embodiments, the nanocomplex is from about 5 nm to about 2000 nm in length as measured along its longest axis. The size may vary depending on the size and number of enzymes in the nanocomplex and the characteristics of the polymer network. In some embodiments, the length of the nanocomplex is at least about 10 nm, 20 nm, 30 nm, 40 nm, 50 nm, 60 nm, 70 nm, 80 nm, 90 nm, 100 nm, 125 nm, 150 nm, 175 nm, 200 nm, 250 nm, 300 nm, 400 nm, or 500 nm. In some embodiment, the length of the nanocomplex is no more than about 50 nm, 60 nm, 70 nm, 80 nm, 90 nm, 100 nm, 125 nm, 150 nm, 175 nm, 200 nm, 250 nm, 300 nm, 400 nm, 500 nm, 600 nm, 700 nm, 800 nm, 900 nm, 1000 nm 1500 nm or 2000 nm.

The nanocomplex can be of any shape, depending on the size, shape and number of the enzymes in the complex. In one embodiment, the nanocomplex is substantially round. In another embodiment, the nanocomplex is substantial oval, spherical, cylinder, or pyramid-like.

In some embodiments, the polymer network is anchored to the enzymes at, collectively, at least 1, 2, 3, 4, 5, 7, 10, 15, or 20 locations. In one embodiment, the polymer network is anchored to at least two of the enzymes. In one embodiment, the polymer network is anchored to each of the enzymes at least at 2, or 3, or 4, or 6 locations. It is contemplated that not every enzyme in the nanocomplex needs to be anchored with the polymer network to effectively constrain the enzyme in the nanocomplex. For instance, for three or more enzymes, when two of them are anchored with the polymer network, the others can be constrained by virtue of their locations relative to the anchored enzymes. Such special constraint can be reinforced by, but does not require, bonding between the enzymes. It is also contemplated that the polymer network can be anchored to just one of the enzymes in the nanocomplex and still effects spatial constraint of the enzymes in the nanocomplex, by virtue of the association of the other enzymes with the one anchored to the polymer network. In one embodiment, the polymer network is anchored to every enzyme in the nanocomplex.

The polymer network can be anchored to the enzymes through any force, such as but not limited to covalent bond, hydrogen bond, ionic force, hydrophobic bonding, and Van der Wall force. In certain embodiments, multiple forces are involved in the anchoring. In some embodiments, not all locations of the anchoring employ the same type of force.

For the purpose of anchoring the polymer network, in one embodiment, two or more enzymes in the nanocomplex have a plurality of polymerizable groups. A polymerizable group is a chemical moiety that polymerizes under certain chemical conditions. Examples of polymerization conditions include photopolymerization, free radical polymerization, and catalyst induced polymerization. In general, the type of polymerizable group is not critical, so long as the polymerizable group is capable of polymerization with a monomer used to form the nanocomplex. Examples of polymerizable groups include double-bond containing moieties which are polymerized by photopolymerization or free radical polymerization. In some embodiments, the polymerizable group is a vinyl group, acryl group, alkylacryl group (i.e. acryl group having an alkyl substituent, such as methacryl). As used herein, acryl (alkylacryl, methacryl, etc) includes acryl t esters as well as acryl amides. In some embodiments, the polymerizable group is an acryl group covalently bonded to a lysine residue of the enzymes.

Enzymes can contain many different surface amino acids which can readily be modified. For example, lysine, cysteine, threonine, glutamic acid, aspartic acid, serine, histidine, arginine, tyrosine, proline and tryptophan may be readily modified using known processes and procedures. A reagent used to modify the protein will have at least one polymerizable group, and at least one reactive group that reacts with an amino acid side-chain on the surface of the protein. Examples of reactive groups that are used to react with amino acid side chains include activated esters (such as acyl halides or N-hydroxysuccinimide esters) that react with amine (such as lysine) and hydroxy 1 (such as threonine or serine) containing residues; maleimides that react with thiol (such as cysteine) containing residues; and amines which react with carboxylic acid (such as glutamic acid and aspartic acid) containing residues when activated with certain coupling reagents. This way, the polymerizable group is covalently bonded to the single-enzymes. The polymerizable group may be directly bonded, or attached through a linker.

Ionic bonds can be used to anchor the polymer network on one or more of the enzymes by virtue of the presence of positive or negative charges of certain amino acids, such as arginine, aspartic acid, glutamic acid, histidine and lysine, and amino acids that are modified to have charges.

In some embodiments, a linker is present between the enzymes and the polymerizable group. The linker is a chemical moiety separating the polymerizable group, and the enzymes. A reagent used as a linker will have at least one polymerizable group, and at least one reactive group separated by a linker. The reactive group reacts with the enzymes, usually by reaction with an amino acid side chain on the surface of the protein, covalently bonding the polymerizable group to the single-enzymes with the linker between them.

In some embodiments, the linker may be degradable. A degradable linker is a chemical moiety that is cleaved under certain conditions. For example, a degradable linker may, for example, hydrolyze at certain pH values (high pH or low pH), or may be cleaved photolytically (i.e. when irradiated with light of certain wavelengths), or under certain temperatures, under reduction-oxidation conditions, or enzymatically (i.e. by proteases). Any suitable degradable linker may be used, so long as the linker has a reactive group to react with the enzymes, and a polymerizable group to form the nanocomplex. The degradable linker should also be stable during polymerization of the nanocomplex. The type of linker may be selected based on the conditions under which the linker will be cleaved. Numerous linkers are known, and will be readily apparent to one of ordinary skill.

Enzymes in these nanocomplexes are more stable than the enzymes in their native, non-complexed forms. Stability is determined in the loss of enzyme activity over time or degradation or denaturation of the enzyme. In some embodiments, the nanocomplexes are resistant to degradation by proteases. The polymer network reduces exposure of the enzymes to proteases. As a result, the activity of the enzymes lasts longer in the presence of proteases (for example, in vivo, in serum, or in cells) than unprotected native enzymes. The polymer network stabilizes the enzyme structure, and prevents aggregation of the enzymes. Thus, the nanocomplexes are more resistant to changes in pH and temperature. For example, nanocomplexes have a longer storage lifetime at room temperature or decreased temperature (i.e. refrigeration or freezing), than the native enzymes. Likewise, nanocomplexes are less likely to lose activity after multiple freeze/thaw cycles than native enzymes. Because the enzymes' structures are stabilized by the polymer network, the nanocomplexes are more resistant to organic solvents and surfactants.

The polymer network may also be adjusted to increase solubility in organic solvents. Examples of organic solvents and surfactants that may be used with the nanocomplexes include methanol, ethanol, isopropyl alcohol, dimethyl sulfoxide, tetrahydrofuran, 4-dichlorobenzene, para-dichlorobenzene, 1,4-dioxane, 1,4-dioxane PEG, polyethylene, polyethylene glycol, polyoxyethylene, sodium laureth sulfate or oxynol, polysorbate 60, 2-bromo-2-nitropropane-1,3-diol, 2-butoxy-1-ethanol, alkyl phenoxy, polyethoxy ethanol, among others widely used in cosmetics (i.e. make-up) and pharmaceuticals. Other organic solvents will be apparent to one of ordinary skill in the art. Because the polymer network prevents aggregation, the nanocomplexes are more stable at interfaces (i.e. gas/liquid or liquid/solid) where unprotected enzymes tend to aggregate.

In some embodiments, the nanocomplex is two or more enzymes co-polymerized with a monomer unit. A monomer unit is a chemical moiety that polymerizes and forms a co-polymer with the single-enzymes, forming the polymer network of the nanocomplex. In some embodiments, when the enzymes bear polymerizable groups having a double bond, such as a vinyl, acryl, alkylacryl or methacryl group, the monomer unit also has a polymerizable group having double bond, such as a vinyl, acryl, acrylamido, alkylacryl, alkylacrylamido, methacryl or methacrylamido group. The polymerizable group of the enzymes, and the polymerizable group of the monomer unit may be the same or different, so long as they are capable of forming a co-polymer under the conditions used to form the nanocomplex. For example, vinyl and acryl groups may form co-polymers under free-radical polymerization conditions.

In some embodiments, the nanocomplex is two or more enzymes co-polymerized with two or more different monomer units. In general, any number of different monomer units may be used to form co-polymers with the enzymes, so long as the different monomer units are all capable of forming a co-polymer under the conditions used to form the nanocomplex. Monomer units with different side-chains may be used to alter the surface features of the nanocomplex. The surface features may be controlled by adjusting the ratio between different monomer units. In some embodiments, the monomers may be neutral, uncharged, hydrophilic, hydrophobic, positively charged, or negatively charged. In some embodiments, the polymer network as a whole is neutral, uncharged, hydrophilic, hydrophobic, positively charged, or negatively charged. Solubility of the nanocomplex may be adjusted, for example, by varying the ratio between charged and uncharged, or hydrophilic or hydrophobic monomer units. In some embodiments, the nanocomplex has a positive or negative charge.

In some embodiments, at least one monomer unit has a positive or negative charge at the physiological pH (~7.4). By using monomer units having a charge at pH=7.4, the overall charge of the nanocomplex may be varied and adjusted by changing the ratio of the charged and uncharged monomer units. In some embodiments, the monomer unit has a positive charge at pH=7.4. Using positively charged monomer units enables the formation of nanocomplexes having a positive charge. The charge may be adjusted by changing the ratio of neutral and positively charged monomer units.

In some embodiments, the polymer network further includes at least a crosslinker. A crosslinker is a chemical compound having two or more polymerizable groups. In general, any crosslinking compound may be used, so long as the polymerizable groups on the crosslinker are capable of forming a crosslinked co-polymer between the enzymes and the at least one monomer unit under the conditions used to form the nanocomplex. Examples of crosslinkers include compounds having two vinyl, acryl, alkylacryl, or methacryl groups. Examples of specific crosslinkers having two acryl groups include N,N'-methylenebisacrylamide and glycerol dimethacrylate.

In some embodiments, the crosslinker is a degradable crosslinker. A degradable crosslinker is cleaved under certain conditions, resulting in decomposition or removal of at least a portion of the polymer network of the nanocomplex. For example, a degradable crosslinker may hydrolyze at certain pH (high or low), may be cleaved by specific enzymes (such as esterases or peptidases), may be photolytically cleaved upon exposure to certain wavelengths, or be cleaved at certain temperatures. Examples of crosslinkers which hydrolyze at reduced pH include glycerol dimethacrylate, which is stable at physiological pH (about 7.4), but hydrolyzes at lower pH (about 5.5). Other examples of degradable crosslinkers include acetal crosslinkers described in U.S. Pat. No. 7,056,901, which is incorporated by reference in its entirety.

Further specific examples of degradable crosslinking groups include N,N'-methylenebis(acrylamide), 1,4-bis(acryloyl)piperazine, ethylene glycol diacrylate, N,N'-(1,2-dihydroxy-ethylene)bisacrylamide, and poly(ethylene glycol)diacrylate. Further examples of non-degradable crosslinking groups include N,N'-bis(acryloyl)cystamine, glycerol dimethacrylate, bis[2-(methacryloyloxy)ethyl] phosphate, and bisacryloylated polypeptide.

In some embodiments, the polymer network is permeable. As used herein, permeable means that molecules (e.g. ethanol) may pass through the polymer network, either through pores or holes in the polymer network, or by diffusion through the polymer matrix. For example, substrates, co-factors and other chemical elements may pass through the polymer network, allowing the nanocomplex to retain the activity of the enzymes inside. In some embodiments of the invention, the polymer matrix is formed from selected constituents and/or under selected conditions designed to generate a matrix having specific permselective properties that influence the diffusion of compounds through the polymer matrix.

A degradable crosslinker can removes or reduces the density of the polymer network and thus allow passing of various objects such as co-factors and the substrates. For example, a degradable crosslinker that decomposes at reduced pH may be used to remove or reduce the polymer coating after the nanocomplexes are internalized into cells by endocytosis. It is well known that serum and late endosomes have pH values of ~7.4 and ~5.5, respectively. Thus, a degradable crosslinker that is stable at pH ~7.4, but degrades at pH ~5.5 will remove or reduce the polymer coating only after the nanocomplex has entered the cell. In this way, the enzymes are protected from proteases present in serum, but enzymes with large substrates may still be effectively delivered to cells. After the polymer coating is reduced, the activity of the enzymes is still present. After the polymer coating is removed, however, the enzymes becomes susceptible to degradation by intracellular proteases, but this drawback is offset by the nanocomplex's increased stability in serum, and resistance to serum proteases.

In certain embodiments, the nanocomplex further includes a surface modification. Surface modifications are chemical moieties which are added to the surface of the nanocomplex after formation of the nanocomplex. Monomer units having reactive sidechains (or protected reactive sidechains) may be used to form the nanocomplex so long as the reactive sidechains do not interfere with formation of the nanocomplex. The reactive sidechains may be (after deprotection, if necessary) reacted with surface modifying agents to covalently attach the surface modification to the nanocomplex. A surface modifying agent may be a small molecule, polymer, peptide, polypeptide, protein, oligonucleotide, polysaccharide, or antibody. The surface modification may alter the solubility of the nanocomplex, change the surface charge of the nanocomplex, or impart an additional function to the nanocomplex, such as light-emission, cell targeting or cell penetration. Surface modifications that enhance cell targeting result in an increased transduction of the nanocomplex into targeted cells, when compared with non-targeted cells. Surface modifications that enhance cell penetration result in increased transduction of nanocomplexes into cells when compared with nanocomplexes lacking the cell penetration enhancer. More than one surface modification may be present on the nanocomplex. Examples of small molecule surface modifications include light emitting compounds, such as fluorescein, or rhodamine, or cell targeting compounds such as folic acid. Polymers include polyethylene glycol to increase solubility. Peptides may be used for cell targeting, such as antibodies to particular cell surface features, cell signaling proteins, or growth hormones. Other peptides may be used to increase cell penetration of the nanoparticles (such as TAT or antennepedia homeodomain). In some embodiments, the surface modification is an antibody.

Methods of Preparing Multiple-Enzyme Nanocomplexes

Multiple-enzyme nanocomplexes of the present disclosure can be prepared by first forming a multiple-enzyme core and then anchoring a polymer network about the core.

1. Preparation of Multiple-Enzyme Core

A method of preparation of a temporary multiple-enzyme core is illustrated in FIG. 1 and described in Example 1. Further details for such an exemplary procedure can be found in Example 2.

In the exemplary method, at a first step, a DNA-inhibitor scaffold is synthesized. As illustrated in FIG. 1, competitive inhibitors for each enzyme are respectively conjugated to a single-strand DNA (ssDNA) with designed sequence; complementary assembly of the DNA molecules forms a DNA-inhibitor scaffold linked with the three inhibitors (see, e.g. Feldkamp et al., Angew Chem Int Edit 45, 1856-1876, (2006)).

Conjugation of a ssDNA with an inhibitor can be achieved with methods known in the art. For example, the conjugation can occur at the 5' phosphate or 5' amineC6T group of the ssDNA (see, e.g., illustration in Example 1 section 3.1).

Figure 5:
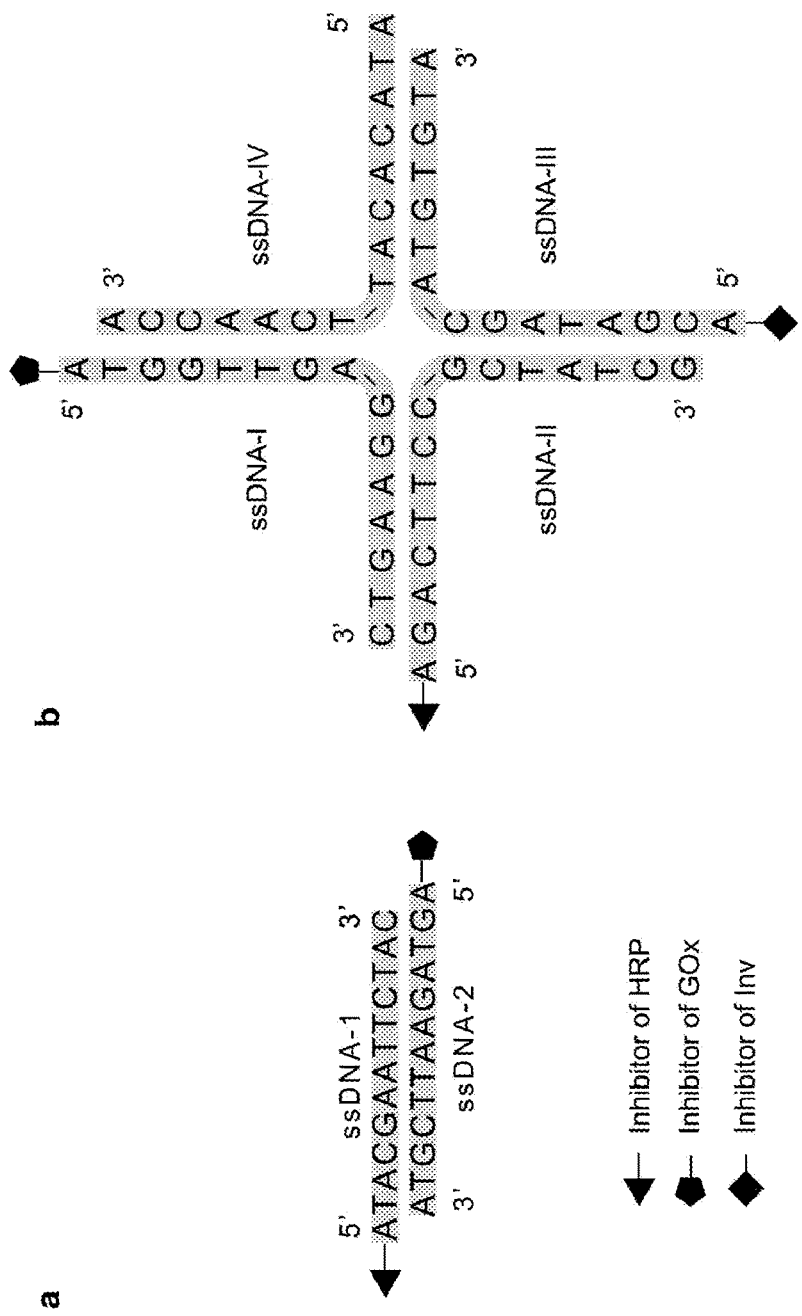
FIG. 5 shows the DNA-inhibitor scaffolds for syntheses of n(HRP-GOx) (a) and n(HRP-GOx-Inv) (b).

Once ssDNA-inhibitors are prepared, the DNA-inhibitor scaffold can be self-assembled owning to the complementary sequences on the ssDNA. FIG. 5a illustrates the assembly of two ssDNA-inhibitor molecules. Therefore, the two ssDNA share a complementary sequence with each other.

In FIG. 5b, on the other hand, the four ssDNA sequences can assemble 3 or 4 inhibitors onto the scaffold. There, ssDNA-I has a sequence that is complementary to a fragment of ssDNA-II, which in turn has a sequence that is complementary to a fragment of ssDNA-III, which in turn has a sequence that is complementary to a fragment of ssDNA-IV, which in turn has a sequence that is complementary to a fragment of ssDNA-I.

The design strategy illustrated in FIG. 5b can be readily applied to form a 5, or 6, or more ssDNA-inhibitor scaffold by including complementary sequences into ssDNA molecules.

Once the multiple-inhibitor scaffold is synthesized, the enzymes can then be bound to the corresponding inhibitor to form an enzyme-inhibitor-ssDNA core.

It is readily appreciated by the skilled artisan that the multiple-enzyme core can be prepared with other methods known in the art. For instance, one or more of the inhibitors can be substituted with an enzyme substrate, ligands, or even an antibody that recognizes the enzyme. The ssDNA, on the other hand, can be replaced by a polymer that anchors the inhibitors, substrates or antibodies.

Also provided, therefore, in one embodiment is a nanocomplex comprising a polymeric scaffold anchored to a plurality of ligands, the ligands recognized by a plurality of enzymes, the enzymes cooperatively react with a substrate. A "ligand" as used herein, broadly intends to cover any molecule that specifically recognizes, or is recognized by, or binds to an enzyme. In one aspect, the polymeric scaffold is a nucleic acid, such as ssDNA. Such polymeric scaffold is useful in preparing multiple-enzyme nanocomplexes, accordingly.

In a further embodiment, the polymeric scaffold further includes the corresponding enzymes.

2. Preparation of Multiple-Enzyme Nanocomplexes

Once a multiple-enzyme core is prepared, a polymer network can be then applied to the core. The polymer network can be anchored covalently, or by other forces describe herein, to two or more of the enzymes derivatizing the enzymes with at least one polymerizable group; and then copolymerizing the derivatized protein with a monomer unit.

An exemplary two-step procedure can be used to form a polymer network about the enzymes. First, polymerizable groups are linked to the enzyme surface. Then subsequent polymerization of functional monomers and optionally, crosslinkers, in buffer solution wraps two or more of the enzymes with a polymer skin.

Once the polymerizable groups are attached to the enzyme surface, monomers can be used to form polymer coatings with tunable composition, structure, surface property, and functionality. A room temperature free-radical polymerization technique may be used to ensure the retention of enzyme activity. Since these polymer coatings serve as artificial membranes for the encapsulated enzymes, they exhibit suitable mechanical strength to provide structural integrity, possess effective transport pathways to allow rapid substrate transport, and contain specific functionality to provide substrate selectivity and moisture retention.

Nanocomplexes do not change the functions of the enzymes, which, as noted above, may be obtained directly from commercial sources or using other reported methods (e.g. recombinant methodologies such as those offered by GENSCRIPT).

A reagent used to derivatize or modify the enzymes has the following general structure where the polymerizable group is a chemical moiety that forms a copolymer with one or more monomers and/or crosslinkers under conditions used to form the nanocomplex. In some embodiments, the polymerizable group is a double bond containing group, such as vinyl, acryl, alkylacryl, and methacryl. As discussed previously, acryl (and alkylacryl and methacryl) includes both acryl esters and acrylamides.

A linking group is optional and may be present between the polymerizable group and the protein. The linking group is a chemical moiety that separates the reactive group from the polymerizable group. The linking group is not limited to any particular chemical structure, but should not interfere in the polymerization reaction. In some embodiments, the linking group is a degradable linking group, which is cleaved under certain conditions. For example, acetals, ketals or esters may be hydrolyzed at certain pHs Linking groups having one or more of these functional groups may decompose in response to changes in pH (e.g. in endosomes).

A reactive group is a chemical moiety that reacts with an amino acid side chain to covalently attach the polymerizable group to the protein. Numerous reactive groups are known and are used to react with different amino acid side chains. For example, acyl halides, or activated esters (such as N-hydroxysuccinimide esters) react with amines (e.g. on lysine) or hydroxyls (e.g. on serine or threonine). Isocyanates react with amines. Epoxides react with amines or thiols (e.g. cysteine). Maleimides react with thiols. Other functional groups may react with amino acid side chains in the presence of one or more coupling reagents (such as carbodiimide reagents). For example amines may react with carboxylic acid amino acid side chains (e.g. on glutamate or aspartate). Other reactive groups will be readily apparent to one of ordinary skill in the art.

During the protein modification mentioned above, to realize the site-specific controlled modification, a genetic recombinant technique can be used to introduce specific amino acids in spatially defined locations. This technique allows precise control of the site and density of the modification.

Examples of specific compounds used to derivatize proteins are known the art, see for instance PCT Application Publication No. WO 2010/104865, the contents of which are incorporated into the present disclosure by reference. This PCT application, furthermore, also discloses details methods of acrylating proteins during the polymerization process, as well as generally preparing protein nanocomplexes.

A monomer unit, in some embodiments, has a side chain and a polymerizable group, where the polymerizable group is a chemical moiety that forms a copolymer with the enzymes and optional crosslinkers under conditions used to form the nanocomplex. Polymerizable groups include all those discussed previously. The polymerizable group of the enzyme, and the polymerizable group of the monomer unit may be the same or different, so long as they are capable of forming a co-polymer under the conditions used to form the nanocomplex. For example, vinyl and acryl groups may form co-polymers under free-radical polymerization conditions.

The side chain is a portion of the monomer unit that does not participate in polymerization. In general, the side chain may have any structure, and may be selected based on the desired properties of the nanocomplex. The side chains of the monomer unit affect the surface properties of the nanocomplex. In some embodiments, the side chain may be neutral, neutral hydrophilic (i.e. water soluble, but not charged), hydrophobic, positively charged, or negatively charged. Neutral side chains include amides, esters, ethers, hydroxyls some of which may be hydrophilic or hydrophobic, depending on their structure. Positively charged side chains include amines (including substituted amines, such as mono and dialkyl amines, and tetrasubstituted ammonium compounds, and cyclic variants thereof), guanidines, and heterocycles such as pyridines and imidazoles. Negatively charged sidechains include carboxylic acids. Hydrophobic side chains include alkyl groups (including linear, branched or cyclic alkyl groups) and aryl groups.

Examples of specific monomer units and their functions include acrylamide (neutral, 1), 2-hydroxyethyl acrylate (neutral, 1), N-isopropylacrylamide (neutral, 2), sodium acrylate (negatively charged, 3), 2-acryloylamido-2-methylpropanesulfonic sodium (negatively charged, 3), allyl amine (positively charged, 4), N-(3-aminopropyl) methacrylamide hydrochloride (positively charged, 4, 5), dimethylamino ethyl methacrylate (positively charged, 5), (3-acrylamidopropyl) trimethylammonium hydrochloride (positively charged, 5), methyl acrylate (hydrophobic, 6) and styrene (hydrophobic 6). The numbers in the parentheses refer to functions: 1 to 5: hydrophilic surface and moisture retention; 2) temperature responsive; 3) negatively charged surface; 4) reactive sidechain for surface modification, 5) positive charge surface, 6) hydrophobic surface.

Polymerization of the modified enzymes and monomer unit(s) may use any method suitable for the polymerizable groups used on the protein and monomer unit(s) and which does not destroy the function of the protein during polymerization. Examples of polymerization methods include photopolymerization and free-radical polymerization of double bond containing polymerizable groups, such as those described previously. In some embodiments, the polymerization is a free radical polymerization.

In some embodiments, the polymerization is carried out at room temperature, though the temperature may be increased or decreased as desired, depending on the polymerization method, so long as the function of the protein is not lost during polymerization. Where degradable crosslinkers or linking groups are used, the function of the nanoparticle may be measured after degradation of the polymer coating. Reaction temperatures may be increased where the polymerization reaction occurs too slowly, or where elevated temperature is needed to initiate polymerization. Temperatures may be decreased where polymerization reactions occur too quickly.

In some embodiments, the polymerization reaction is performed in water, or aqueous buffer. Other solvents may be used as desired, so long as the solvent does not interfere with the polymerization reaction, or degrade the protein. Mixtures of water or aqueous buffer and organic co-solvents may also be used, if necessary to dissolve reaction components, so long as the solvent mixture does not interfere with the reaction, or damage the enzymes. In some embodiments, the polymerization reaction is performed in buffer.

In some embodiments, the copolymerization step comprises at least two different monomer units. In general, any number of different monomer units may be used to form copolymers with the enzymes, so long as the different monomer units are all capable of forming a co-polymer under the conditions used to form the nanocomplex. Monomer units with different side-chains may be used to alter the surface features of the nanocomplex. The surface features may be controlled by adjusting the ratio between different monomer units. In some embodiments, the monomer may be neutral, neutral hydrophilic, hydrophobic, positively charged, or negatively charged. Solubility of the nanocomplex may be adjusted by varying the ratio between charged and uncharged, or hydrophilic or hydrophobic monomer units.

In some embodiments, the copolymerization step further includes a crosslinker. A crosslinker is a reagent having at least two polymerizable groups, separated by a linking group. The crosslinker may have more than two polymerizable groups. The polymerizable groups on the crosslinker may be the same or different, so long as all the polymerizable groups on the crosslinker are able to form a copolymer with the monomer unit(s) and enzymes under the conditions used to form the nanocomplex. A crosslinker having two polymerizable groups has the general structure where the polymerizable groups are the same as those described previously. The linking group may have any structure so long as it does not interfere with the polymerization reaction. Examples of suitable linkers include alkyl groups (including substituted alkyl groups), aryl groups (including substituted aryl groups), ketones, amides, esters, ethers and combinations thereof. Specific examples of crosslinkers include N,N'-methylene bisacrylamide and glycerol dimethacrylate and others as described above.

In some embodiments, the linking group is degradable. A degradable linking group may be cleaved under certain conditions. The structure of the degradable linking group determines the type of conditions required to cleave the linking group. For example, the linking group may be cleaved due to a change (i.e. increase or decrease) in pH, exposure to certain wavelengths of light, or in response to heat. An example of a degradable crosslinker is glycerol dimethacrylate.

In some embodiments, the method of producing a nanocomplex further includes a step of modifying the surface of the nanocomplex. Sidechains of the monomer unit(s) are present on the surface of the nanocomplex after polymerization. Monomer units having a reactive sidechain (or protected reactive sidechain) may be used to prepare the nanocomplex. The reactive sidechain does not interfere with polymerization, but may undergo further chemical modification after the nanocomplex is formed (i.e. after polymerization is completed). A protected reactive sidechain may be deprotected using standard chemical deprotection methods, then reacted with a chemical modifying agent. A reactive sidechain is treated with a chemical reagent to covalently attach the surface modifying agent to the surface of the nanocomplex. The surface modification may be a small molecule, polymer, peptide, polypeptide, protein, oligonucleotide, polysaccharide, or antibody. The surface modification may alter the solubility of the nanocomplex (e.g. by adding polyethylene glycols or other hydrophilic groups), change the surface charge of the nanocomplex (e.g. by adding charged surface modifiers), or impart an additional function to the nanocomplex, such as light-emission, cell targeting or cell penetration. Examples of small molecule surface modifications include light emitting compounds, such as fluorescein, or rhodamine, or cell targeting compounds such as folic acid. Polymers include polyethylene glycol to increase solubility. Peptides and polypeptides may be used for cell targeting, and may include antibodies selective to specific cell surface features, cell signaling peptides, or hormones. Other peptides may be used to increase cell penetration of the nanoparticles (such as TAT or antennepedia homeodomain). In some embodiments, the surface modification is an antibody. Because nanocomplexes have an easily derivatizeded surface, specific antibodies can be conjugated with nanocomplexes providing extra ability of targeting delivery.

The size and surface features of the nanocomplexes may be adjusted by varying the weight ratio of the different monomers and/or crosslinkers used to form the nanocomplex. For example, tuning the weight ratio of DMAEMA (positive charged) to AAm (neutral) from 0:1, 1:3 and 1:1 allows the synthesis of BSA nanocomplexes with adjustable zeta potentials from −12.8, 8.64 to 15.2 mV, respectively. Solubility may also be easily adjusted by changing the types and ratios of monomer units and crosslinkers. Increasing the amount of hydrophilic or charged monomers increases water solubility. Increasing the amount of hydrophobic monomers tends to increase nanocomplex solubility in organic solvents or mixed organic/water solvent systems.

The permeability of the polymer network may be adjusted by varying the ratio of the crosslinker in the reaction mixture used to prepare the nanocomplex. In general, a lower amount of crosslinker results in a higher permeability. Likewise, the permeability of the polymer network may be varied by changing the length of the linking group on the crosslinker. Generally, longer linking groups lead to increased permeability.

After the multiple-enzyme core is anchored to a polymer network, the ssDNA-inhibitor scaffold, or any other kind of scaffold that serves the purpose of temporally maintaining the core, can be removed. Removal of the scaffold can be done by a condition or reagent that dissociates the inhibitors from the enzymes, so long as such condition or reagent does not disrupt the anchoring of the polymer network at the enzymes. Examples of such conditions and reagents are provided in the examples and are readily recognized by the skilled artisan.

Uses

The enzyme nanocomplexes described herein may be used to carry out a series of enzymatic functions in a concerted manner with increased efficiency, increased stability, and reduced production of intermediates. In the event one or more the intermediates are toxic, the enzyme nanocomplex also reduces or eliminates the release of the toxic intermediates. The specific use of the enzyme nanocomplex depends on what enzymes are enclosed in the complex.

Further, the enzyme nanocomplexes can also be used to deliver the enzymes to a cell in vitro or in vivo with improved stability and/or long-term effect. Since the nanocomplexes are more resistant to degradation by proteases, the protein activity has a longer effect than when native or unprotected proteins are administered. As a result, less enzymes (in the form of nanocomplexes) is required for the same effect (when compared with unprotected proteins), thereby improving efficiency.

Embodiments of the invention include a method of delivering enzymes by exposing a cell to an effective concentration of nanocomplexes described above. The cells may be in culture (i.e. in vitro) or may be present in a living organism (i.e. in vivo).

In some embodiments, at least one of the enzymes is a therapeutic enzyme. A therapeutic enzyme is one that can be used to treat a disease or disorder in a subject. In some embodiments, the subject is a mammal, or a human.

The nanocomplexes described herein may be used with enzymes that may be used to treat a disease or disorder in a subject. For example, nanocomplexes according to the invention may be used in the treatment of a hyperproliferative disorder, cancer, or tumor. In other embodiments, the nanocomplexes may be used in cosmetics.

Furthermore, since such an enzyme nanocomplex is more stable, than their isolated forms, in high temperature and acidic and basic conditions, such an enzyme nanocomplex certainly shows greatly improved use.

Pharmaceutical Compositions

The nanocomplexes discussed herein can be formulated into various compositions, for use in diagnostic or therapeutic treatment methods. The compositions (e.g. pharmaceutical compositions) can be assembled as a kit. Generally, a pharmaceutical composition of the invention comprises an effective amount (e.g., a pharmaceutically effective amount) of a composition of the invention.

A composition of the invention can be formulated as a pharmaceutical composition, which comprises a composition of the invention and pharmaceutically acceptable carrier. By a "pharmaceutically acceptable carrier" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18$^{th}$ ed., Mack Publishing Company, 1990. Some suitable pharmaceutical carriers will be evident to a skilled worker and include, e.g., water (including sterile and/or deionized water), suitable buffers (such as PBS), physiological saline, cell culture medium (such as DMEM), artificial cerebral spinal fluid, or the like. A pharmaceutical composition or kit of the invention can contain other pharmaceuticals, in addition to the compositions of the invention. The other agent(s) can be administered at any suitable time during the treatment of the patient, either concurrently or sequentially.

One skilled in the art will appreciate that the particular formulation will depend, in part, upon the particular agent that is employed, and the chosen route of administration. Accordingly, there is a wide variety of suitable formulations of compositions of the present invention.

One skilled in the art will appreciate that a suitable or appropriate formulation can be selected, adapted or developed based upon the particular application at hand. Dosages for compositions of the invention can be in unit dosage form. The term "unit dosage form" as used herein refers to physically discrete units suitable as unitary dosages for animal (e.g. human) subjects, each unit containing a predetermined quantity of an agent of the invention, alone or in combination with other therapeutic agents, calculated in an amount sufficient to produce the desired effect in association with a pharmaceutically acceptable diluent, carrier, or vehicle.

One skilled in the art can easily determine the appropriate dose, schedule, and method of administration for the exact formulation of the composition being used, in order to achieve the desired effective amount or effective concentration of the agent in the individual patient.

The dose of a composition of the invention, administered to an animal, particularly a human, in the context of the present invention should be sufficient to effect at least a detectable amount of a diagnostic or therapeutic response in the individual over a reasonable time frame. The dose used to achieve a desired effect will be determined by a variety of factors, including the potency of the particular agent being administered, the pharmacodynamics associated with the agent in the host, the severity of the disease state of infected individuals, other medications being administered to the subject, etc. The size of the dose also will be determined by the existence of any adverse side effects that may accompany the particular agent, or composition thereof, employed. It is generally desirable, whenever possible, to keep adverse side effects to a minimum. The dose of the biologically active material will vary; suitable amounts for each particular agent will be evident to a skilled worker.

Another embodiment of the invention is a kit useful for any of the methods disclosed herein, either in vitro or in vivo. Such a kit can comprise one or more of the compositions of the invention. Optionally, the kits comprise instructions for performing the method. Optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form.

EXAMPLES

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

Terms listed in single tense also include multiple unless the context indicates otherwise.

The examples disclosed below are provided to illustrate the invention but not to limit its scope. Other variants of the invention will be readily apparent to one of ordinary skill in the art and are encompassed by the appended claims. All publications, databases, and patents cited herein (e.g. U.S. Pat. No. 6,153,217; U.S. Patent Application Publication No. 20090060894; International Application Number PCT/US2012/33515 filed Apr. 13, 2012 for: REDOX RESPONSIVE POLYMERIC NANOCAPSULES FOR PROTEIN DELIVERY) are hereby incorporated by reference for all purposes.

Methods for preparing, characterizing and using the nanocomplexes of this disclosures are illustrated in the following Examples. Starting materials are made according to procedures known in the art or as illustrated herein. The following examples are provided so that the invention might be more fully understood. These examples are illustrative only and should not be construed as limiting the invention in any way.

Example 1: Design of Highly Robust Artificial Enzyme Nanocomplexes (ENS) with Synergic Function This example demonstrates a general design of highly robust artificial enzyme nanocapsules (ENs) with synergic function. This is achieved by assembling or conjugating enzymes with synergic or complementary functions, or enzymes that can cooperatively function together, into a nanocomplex, followed by encapsulating the nanocomplex within a network-polymer capsule.

Methods

Synthesis of Enzyme Nanocomplexes (ENs): The synthesis of DNA-inhibitor scaffolds was achieved by conjugating the inhibitors to single-strand DNA (ssDNA) with designed sequence followed by their spontaneous assembly to form the scaffold. Briefly, 10 mg of 1-ethyl-3-(3-dimethylaminopropyl) carbodiimide (EDAC) and 60 μL of 5'-phosphated ssDNA (5 nmol/μL) were mixed, followed by addition of 50 μL of enzyme inhibitor (0.2 M) or substrate derivatives (dissolved in 0.1M imidazole MES buffer). The mixtures were then mixed thoroughly by vortexing. After centrifugation for 5 min at 8000 rpm, the mixtures were kept at room temperature for 2 h to allow a complete reaction. As-conjugated ssDNA was then purified by gel filtration on desalting resin using EDTA-phosphate buffer (10 mM sodium phosphate, 0.15 M NaCl, 10 mM EDTA, pH=7.4). Complementary ssDNA-inhibitor molecules were then mixed, incubated at 37° C. for 10 min, and cooled to room temperature to form the DNA-inhibitor scaffolds.

To synthesize n(HRP-GOx), GOx and HRP were anchored with acryloyl groups by reacting with acrylic acid N-hydroxysuccinimide ester (NAS) in 20 mM sodium carbonate buffer (pH=8.5) for 2 h. After dialysis against phosphate buffer (20 mM, pH=7.0), acryloxylated HRP, acryloxylated GOx, and DNA-inhibitor scaffold (1.5:1.5:1, n/n/n) were mixed and kept at room temperature for 20 min to form the enzyme-scaffold complexes. The complexes were then encapsulated by in-situ polymerization using acrylamide (4:1 weight ratio to all enzymes) as the monomer, bis-methylacrylamide (1:6 weight ratio to acrylamide) as the cross-linker, and ammonium persulfate/tetramethylethylenediamine as the initiator. The encapsulated complexes were firstly purified by dialysis against PBS, then heated to 37° C. for 10 min and further purified using size exclusion chromatography (Sepharose 6B). The synthesis of n(HRP-GOx-Inv), n(GOx-Cat), n(AOx-Cat), n(Cat), n(AOx), n(GOx) and other enzyme nanocapsules were conducted using a similar approach and the details are provided in Example 2. Detailed characterization of the ENs, including dynamic light scattering (DLS), transmission electron microscopy (TEM), fluorescent microscopic images and spectra, cell viability assays, toxicity, and other related information are also provided in Example 2.

In-vivo studies: In-vivo studies of alcohol antidotes were achieved by monitoring the variation of blood alcohol concentration (BAC) and the level of plasma alanine aminotransferase (ALT) of mice after treating with ethanol, native enzyme, and enzyme nanocapsules. Four groups of enzyme nanocapsules, including n(AOx), n(Cat), mixture of n(AOx) and n(Cat), and n(AOx-Cat) with the same enzyme content were used. Native AOx was used for comparison. Male C57B6 mice of 8-10 week old from Jackson Laboratory (Bar Harbor, Me.) were used for the studies. Mice were fasted for 8-12 hours, followed by gavage with the enzyme nanocapsules and native AOx or nanocapsules (dosed at 65 μg AOx/animal) within the alcohol-containing liquid diet (AIN76A, Dyets Inc., dosed at 6 g of EtOH/kg body weight (w/w)). For the control group of mice, isocaloric diet without EtOH were fed via gavage. Blood samples were taken from tails at 45, 90, 180 and 360 min after the alcohol gavage. BACs of the alcohol-fed animals were determined using an ethanol assay kit (BioVision). Background BAC was deducted by using control mice gavaged with 250 μL of PBS buffer only. ALT values in the plasma of mice were determined at six to eight hours after the alcohol gavage by following methods described in Ji et al., *Gastroenterology* 124:1488-99 (2003). All animals were treated in accordance with the Guide for Care and Use of Laboratory Animals approved by local committee.

In-vivo detoxification capability of n(GOx-Cat) was conducted using Male mice (C57B6). The mice were anesthetized using ketaime (85 mg/kg) combined with xylazine (10 mg/kg), which were intramuscularly injected into the posterior thighs. Hairs on the back of animals were then removed using an animal shaver. n(GOx), n(Cat) and n(GOx-Cat) were delivered into the skin via two cutaneous injections, respectively, at 0 and 24 hours with a dosage of 35 μg nanocomplex dispersed in 50 μl PBS buffer per group per injection. Equal volumes of hydrogen peroxide ($H_2O_2$) solution (3% w/v) and PBS buffer were injected at different spots of the back of the same animals, respectively, as the positive and negative controls. The animals were anesthetized at 24 hours following the second injection; pieces of skin tissues were then sampled, fixed and processed for H&E staining and for fluorescent TUNEL staining using an in situ Cell Death Detection Kit from Roche. H&E images were captured with a Nikon Eclipse E600 microscope and confocal fluorescence images were obtained with a Nikon PCM2000 confocal laser-canning microscope according to Ji et al., *Hepatology* 40:442-51 (2004).

Results

As illustrated in FIG. 1, competitive inhibitors for each enzyme are respectively conjugated to a single-strand DNA with designed sequence; complementary assembly of the DNA molecules forms a DNA-inhibitor scaffold linked with the three inhibitors; specific bindings of the inhibitors and the enzymes construct the triple-enzyme nanocomplexes (Step I).

Subsequent in-situ polymerization grows a thin layer of network polymer around each nanocomplex, leading to the formation of nanocomplexes containing a triple-enzyme core and a permeable shell (Step II). Finally, removal of the DNA-inhibitor scaffolds creates highly robust ENs denoted as n(Enzymes), where Enzymes within the parentheses refer to the enzymes within the core of the nanocomplexes (Step III). It is important to point out that encapsulating the enzymes within the nanocomplexes effectively stabilizes them against non-physiological environment and protease attack, furthermore, as-formed nanocomplexes can be readily functionalized to acquire desired surface properties and targeting capability (see, e.g. Yan et al., Nat Nanotechnol 5, 48-53, (2010)).

Figures 6A, 6B:
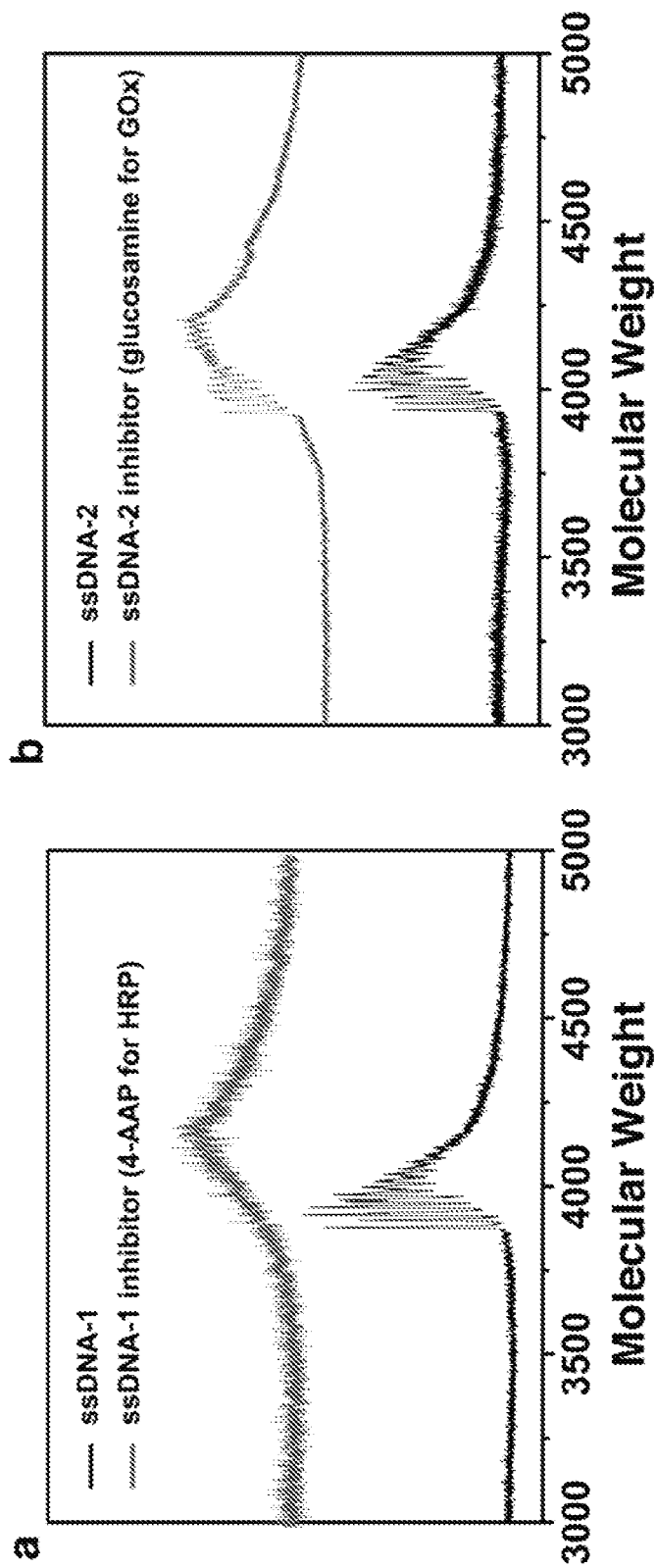
FIG. 6 shows MALDI-TOF mass spectra of DNAs before (black) and after (gray) 5'-modification with inhibitors. (a) ssDNA-1 and 4-Aminoantipyrine (4-AAP) modified ssDNA-1. (b) ssDNA-2 and glucosamine modified ssDNA-2. (c) ssDNA-I and glucosamine modified ssDNA-I. (d) ssDNA-II and 4-AAP modified ssDNA-II. (e) ssDNA-III and lactobionic acid modified ssDNAIII. (f) ssDNA-IV.
Figures 6C, 6D:
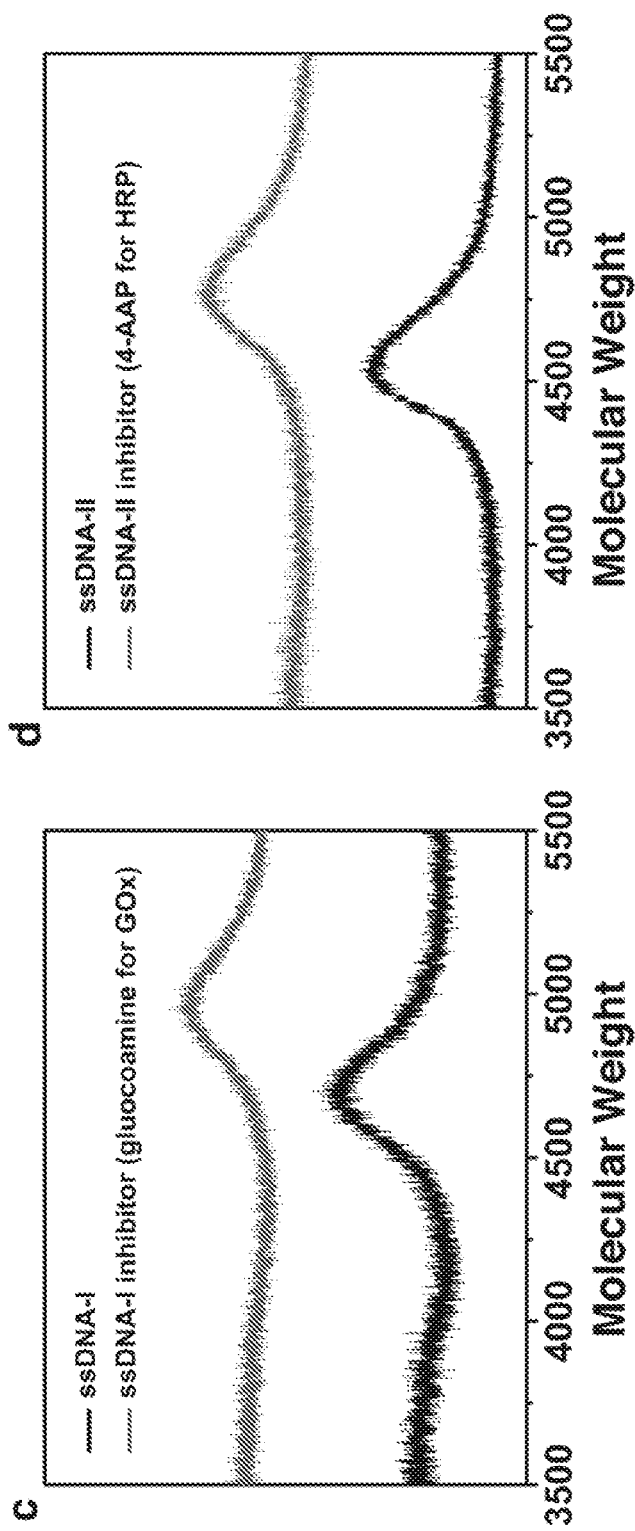
Figures 6E, 6F:
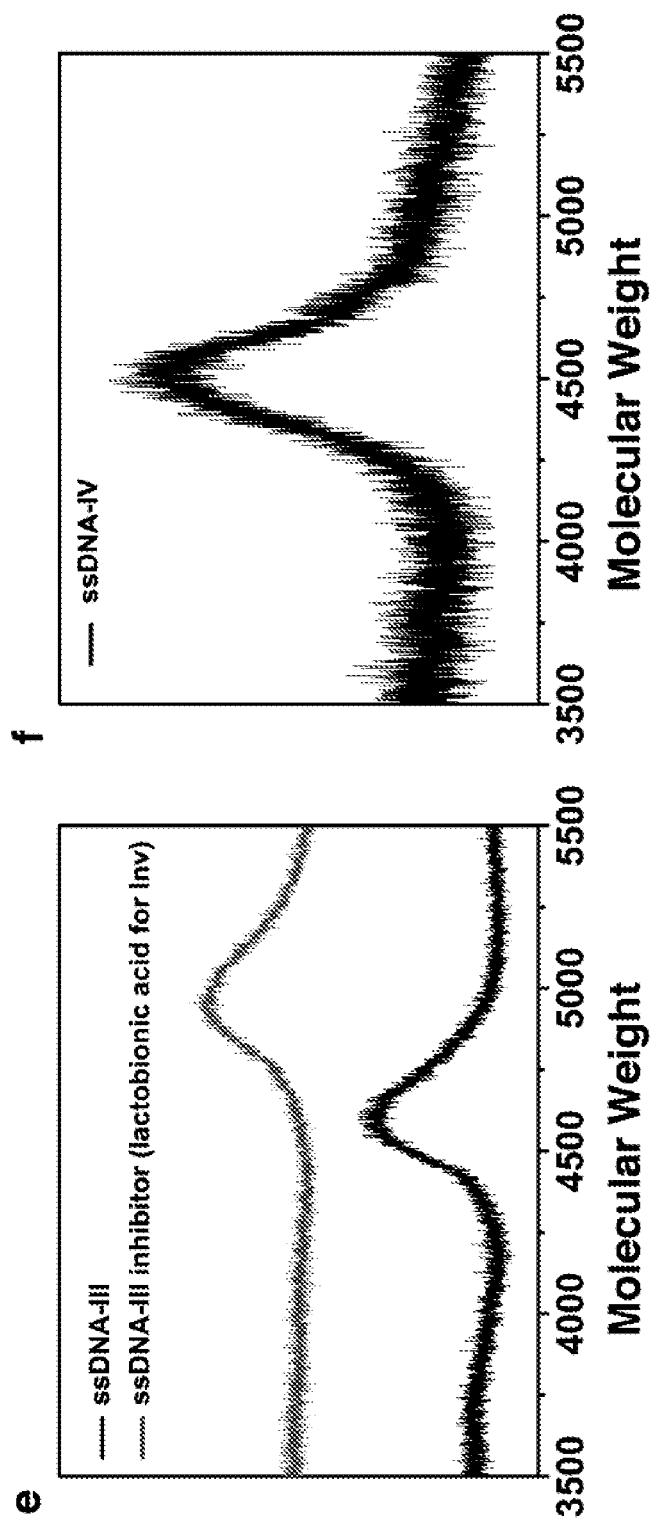

Successful construction of the ENs architecture was demonstrated using horseradish peroxidase (HRP) and glucose oxidase (GOx) as the model enzyme. FIG. 2a shows a Transmission electron microscopic (TEM) image of n(HRP-GOx) with an average diameter of 30±7 nm, which is confirmed by dynamic light scattering (DLS) measurement (FIG. 6). To confirm the double-enzyme architecture, each HRP and GOx molecule was labeled with a single 1.4-nm gold nanoparticle prior to the ENs construction. As shown in FIG. 2b, most gold-labeled ENs contain two gold nanoparticles, indicating that each EN indeed contains one HRP and one GOx molecule accounting specific bindings between the inhibitor and the enzyme.

Such nanocomplex architecture spatially defines the constituent enzymes within close proximity. Using Rhodamine-B-labeled HRP (HRP-RhB) and fluorescein-isothiocyanate-labeled GOx (GOx-FITC) as an example, FIG. 2c compares the fluorescence spectra of their mixture (equal molar ratio) and the corresponding dual-enzyme ENs with the same enzyme content. Since FITC and RhB possess excitation maximums at 495 and 540 nm, respectively, the mixture only exhibits the FITC emission centered at 520 nm under 450 nm excitation. For comparison, the ENs exhibit intense emissions from both FITC and RhB (centered at 520 nm and 585 nm, respectively), indicating an effective Foster resonance energy transfer (FRET) from GOx-FITC to HRP-RhB. This observation clearly confirms that HRP and GOx are closely associated within a short distance (<10 nm) (see, e.g. Selvin et al., Nat Struct Biol 7, 730-734, (2000)). To further confirm the close-proximity structure, FIG. 2d shows fluorescence microscopic images of the ENs, exhibiting clear co-localization of GOx-FITC and HRP-RhB. Upon excitation at 488 nm, FRET emission at 580 nm was also recorded at the same position, further validating the close proximity architecture.

As observed, such close-proximity architecture endows the ENs with significantly enhanced catalytic efficiency. This was demonstrated by consecutive reactions of sucrose and glucose mediated by invertase (Inv), GOx and HRP. Glucose directly added in the reaction media or generated from the Inv-mediated hydrolysis of sucrose is oxidized via the GOx-mediated reaction, leading to the production of $H_2O_2$. As-produced $H_2O_2$ further oxidizes o-dianisidine via the HRP-mediated reaction, which is used to probe the overall enzymatic reaction efficiency.

FIG. 2f compares the turnover rates (o-dianisidine oxidation rates) of n(HRP-GOx) and n(HRP-GOx-Inv) with those of their native enzyme mixtures with the same enzyme contents. Compared with the native enzyme mixtures, n(HRP-GOx) and n(HRP-GOx-Inv) show enhanced turnover rate by 5 and 15 folds in buffer solution, respectively, confirming an enhanced catalytic efficiency. To simulate the viscous environment within the cells or blood stream 9 see, e.g. Ellis et al., Trends Biochem Sci 26, 597-604, (2001)), polyethylene glycol (PEG, Mw~3000) was added to the reaction media to increase the viscosity (diffusion resistance of intermediates within the media). As expected, n(HRP-GOx) systematically exhibits increased relative turnover rates with increasing PEG concentration; 34 fold increase in turnover rate was achieved in the presence of 35 wt-% PEG. Similarly, n(HRP-GOx-Inv) shows up to 24-fold enhancement in relative turnover rates in PEG solutions. The significantly improved rates of the chemical transformations are attributed to the close-proximity architecture that effectively minimizes diffusion of the intermediates. Besides the enhanced catalytic efficiency, n(HRPGOx) and n(HRP-GOx-Inv) also exhibit significantly enhanced stability.

FIG. 2e compares the residual enzyme activities of n(HRP-GOx) and n(HRP-GOx-Inv) with their enzyme-mixture counterparts. n(HRP-GOx) and n(HRP-GOx-Inv) retain 70% and 75% of their original activities after incubation at 65° C. for 60 minutes, whereas the mixtures lose more than 98% activities.

The capability of making ENs with significantly enhanced activity and stability offers a novel class of enzyme machineries for bio-catalysis, sensing, therapeutic and other applications. Oxidases, for example, are being used or proposed for many therapeutic applications such as the treatment of gouts (see, e.g. Sherman et al., Adv Drug Deliver Rev 60, 59-68, (2008); Schelsinger et al., Nat Rev Drug Discov 10, 17-18, (2011); Sundy et al., Arthritis Rheum 58, 2882-2891, (2008); and Kehrer et al., Crit Rev Toxicol 23, 21-48, (1993)).

Figure 3:
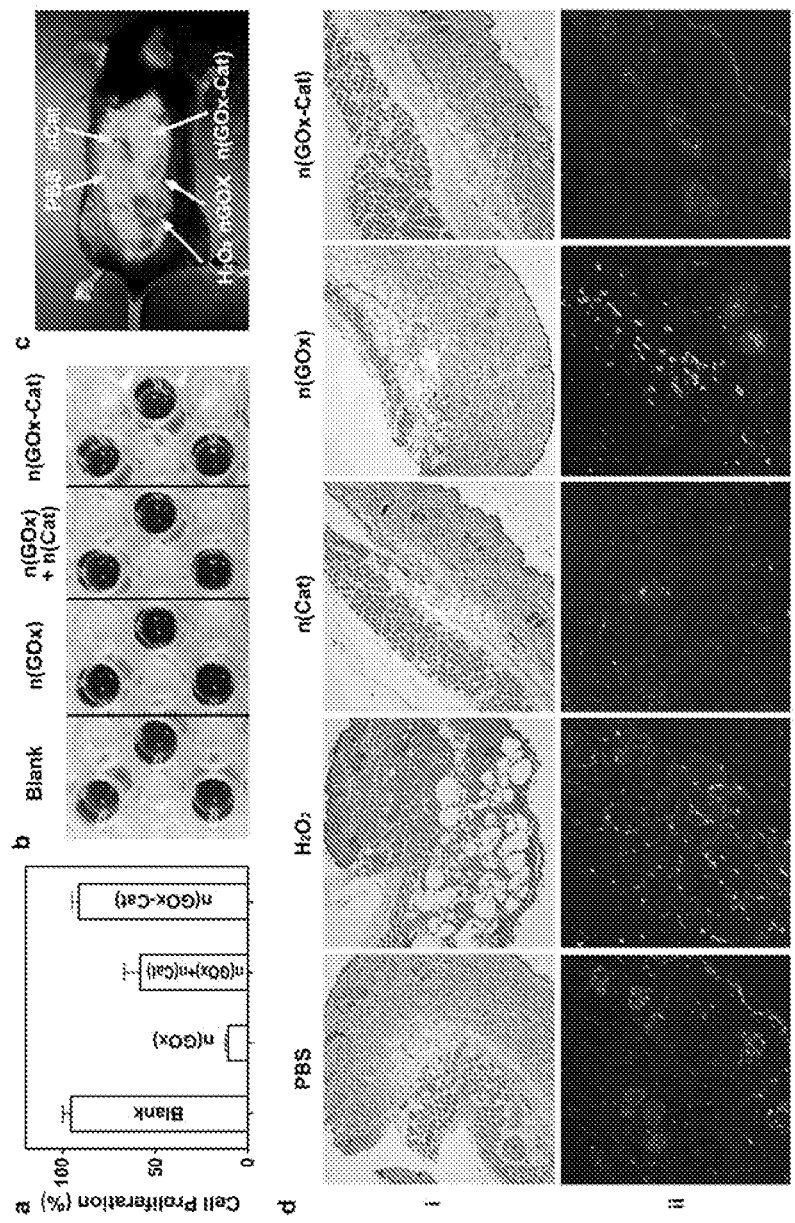
FIG. 3 presents the in vivo detoxifying capability of Catalase-containing enzyme nanocomplexes. (a & b) Cell viability assays after treated with n(GOx), mixture of n(GOx) and n(Cat), and n(GOx-Cat). Cell proliferation rates were normalized with those of the untreated cells. Cell viability assays were performed by incubating the treated cells with CellTiter Blue for 3 h at 37° C., where the viable cells reduced CellTiter Blue exhibiting a highly fluorescent reddish color. (c&d) Photograph of a mouse cutaneously injected with PBS, n(Cat), $H_2O_2$, n(GOx), and n(GOx-Cat) at different sites and the corresponding skin tissue slices obtained from each of the injecting sites: (i) Hematoxylin and eosin (H&E) staining of skin tissue slices of mice (original magnification 40x). (ii) Cell apoptosis in mouse skin tissue slices. Apoptosis was determined by TUNEL staining (green) identified with Cy3-conjugated monoclonal α-smooth muscle actin antibody (red). DAPI was used for nuclear staining (blue). The immunostained slices were evaluated and photographed with fluorescence microscopy (original magnification 200×).

Nonetheless, oxidase-mediated reactions generally produce toxic $H_2O_2$, which may cause damages to organs and tissues (see, e.g. Kehrer et al., Crit Rev Toxicol 23, 21-48, (1993)). Fortunately, this limitation can be effectively addressed using the EN technology. Exemplified by n(GOx), its incubation with cells leads to a loss of 90% cell viability owning to the $H_2O_2$ generated from GOx-mediated glucose oxidation (FIG. 3a). Adding n(Cat) into the culture media effectively reduces the cell viability loss (58%) due to catalase-mediated decomposition of the $H_2O_2$. Amazingly, n(GOx-Cat) far outperforms the mixture of n(GOx) and n(Cat) (with same enzyme content). Cells treated with n(GOx-Cat) show similar viability to that of the untreated cells (91%). FIG. 3b shows photographs of the cells cultured with n(GOx), mixture of n(Cat) and n(GOx), and n(GOx-Cat) with the same enzyme content after treating with CellTiter Blue for 3 h at 37° C. Consistently, the cells cultured with n(GOx-Cat) show a much intense reddish fluorescent color than others, indicating a higher cell viability due to more effective $H_2O_2$ elimination. Without being bound by a specific scientific theory or mechanism of action, this observation is consistent with an unexpected phenomena, one where the close-proximity enzyme architecture not only enhances the overall chemical-transformation efficiency, it also furthers the effective removal of toxic intermediates so as to avoid potential cell and tissue damages.

To further confirm the in-vivo detoxification capability of ENs, n(GOx), n(Cat) and n(GOx-Cat) were injected cutaneously to a mouse (C57BL/6) at different injection sites. As positive and negative controls, equal volumes of $H_2O_2$ solution (3% w/v) and PBS vehicle were injected to separate skin sites of the same mouse, respectively Skin lesions were observed in $H_2O_2$-treated and n(GOx)-treated sites 48 hours after injection.

In contrast, skin damages were not observed in the spots injected with PBS, n(Cat), or n(GOx-Cat) (FIG. 3c). For further toxicity studies, the mouse was sacrificed and skin tissues at the injection sites were sectioned and stained with hematoxylin and eosin (H&E) and TUNEL staining kit. Clearly, $H_2O_2$ administration caused tearing and ballooning in the dermis of the skin; n(GOx) administration caused similar tissue ballooning and neutrophil infiltration albeit to a smaller extent, indicating pathophysiological response and injury due to the $H_2O_2$ generated (FIG. 3d). Cell apoptosis was evident in the skin tissues treated with either $H_2O_2$ or n(GOx), whereas the cell death in n(Cat) or n(GOx-Cat) treated skin tissues was minimal and was comparable to that of PBS treated sample (FIG. 3d).

These observations clearly demonstrated that, by encapsulating GOx and Cat in close proximity within the ENs, one could effectively reduce the toxicity and tissue damage associated with the administration of oxidases, which shines light on the current oxidase-related therapeutics.

Further therapeutic significance of this technology was demonstrated by ENs of catalase and alcohol oxidase, a potential antidote for alcohol. Alcohol consumption is a millennium-old component of human civilization; alcohol abuse, however, associates with a series of organ injuries (e.g., liver damage) and social problems (e.g., violence and driving under influence of alcohol (DUI) see, e.g. Lee et al., Lancet 2, 759-761, (1979)). Biologically, metabolic process of alcohol relies on consecutive actions of alcohol dehydrogenase (conversion of ethanol to acetaldehyde) and acetaldehyde dehydrogenases (conversion of acetaldehyde to acetic acid) mediated by nicotinamide adenine dinucleotide (NAD+) (see, e.g. Crabb et al., P Nutr Soc 63, 49-63, (2004)).

However, low extracellular NAD+ concentration restricts the use of such dehydrogenases as extracellular antidotes (see, e.g. Ji et al., Hepatology 40, 442-451, (2004)). To circumvent this limitation, we designed a novel enzymatic machine based on n(AOx-Cat), where AOx is alcohol oxidase that can effectively mediate oxidization of alcohol to acetaldehyde using molecular oxygen.

Figure 8:
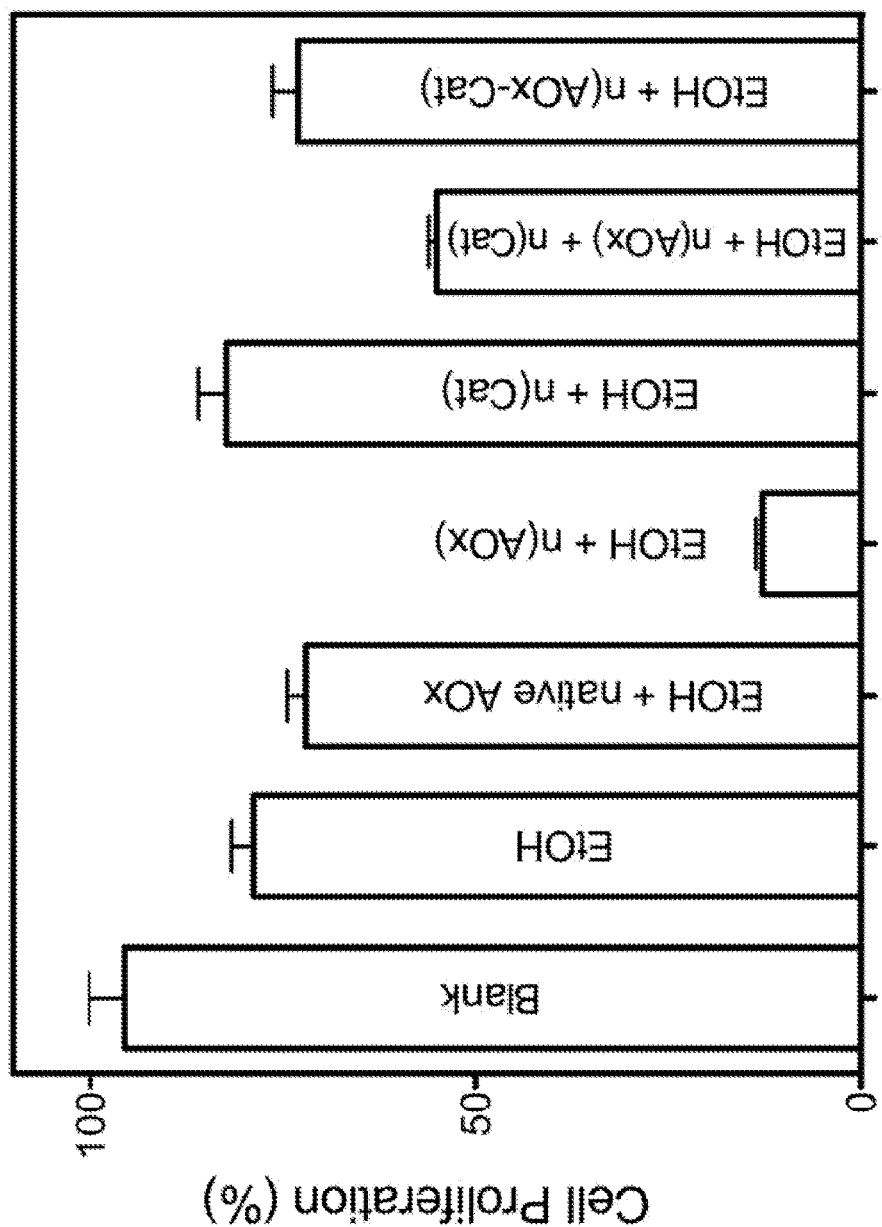
FIG. 8 shows the viability of cells treated with EtOH and n(AOx-Cat) in comparison with native AOx and mixture of n(AOx) and n(Cat).

Similar to other oxidase, this oxidation process also produces toxic byproduct $H_2O_2$; nevertheless, as-produced $H_2O_2$ can be promptly eliminated by the catalase proximately located within the ENs (see cell viabilities in FIG. 8). It is also important to point out that, both AOx and Cat encapsulated within the n(AOx-Cat) are well protected by the polymer shells from protease attack and non-physiological condition, enabling their versatile administration orally and systematically.

Figure 4:
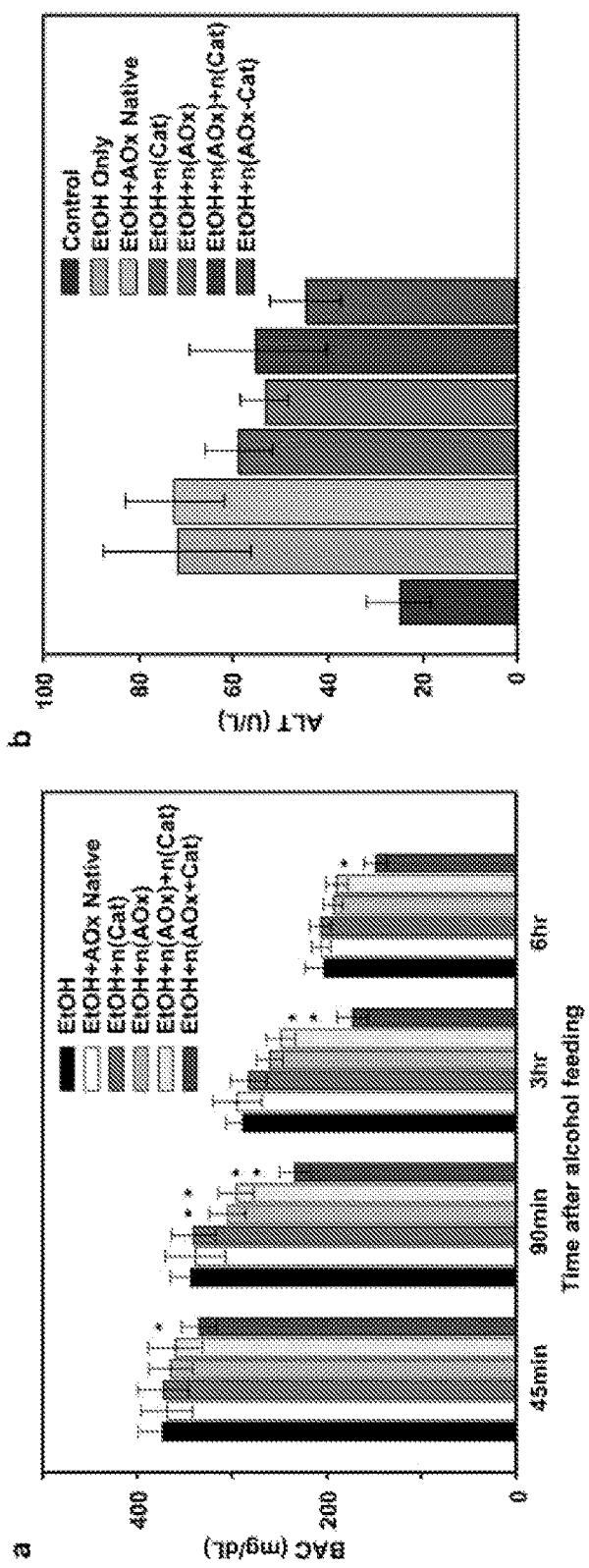
FIG. 4 presents comparison charts to demonstrate the efficacy of Oral n(AOx-Cat) Alcohol Antidote. (a) Blood alcohol concentration (BAC) in mice after gavage with alcohol only, and alcohol along with native AOx, n(Cat), n(AOx), a mixture of n(AOx) and n(Cat), or n(AOx-Cat). BAC was determined with an alcohol test kit. For mice treated with n(AOx-Cat), BAC decreases remarkably within 3 hr (*$P<0.05$; **$P<0.01$) compared to mice fed alcohol only (EtOH). Four mice were used in each group. (b) Corresponding plasma alanine aminotransferase (ALT) of the mice. Mice in the control group were fed with normal food, other groups of mice were gavaged with a liquid diet containing ethanol along with PBS, native AOx, n(Cat), n(AOx), a mixture of n(AOx) and n(Cat), or n(AOx-Cat).

FIG. 4 demonstrates efficacy of oral alcohol antidotes based on n(AOx-Cat). Mice were gavaged with a liquid diet containing alcohol together with native AOX, n(AOX), n(Cat), an equal-ratio mixture of n(AOx) and n(Cat), or n(AOx-Cat). All the animals were under alcohol intoxication and slept within 20 minutes after the alcohol administration; average blood alcohol concentration (BAC) in mice with alcohol diet was 374±25.8 mg/dL 30 min after the administration. Compared with the mice administrated with alcohol only, the BAC of the mice administrated with n(AOx-Cat) was reduced by 10.1%, 31.8% and 36.8% at 45 min, 90 min and 3 hours after injection, respectively (FIG. 4a). Only slight BAC reductions during these periods were observed in those administrated with n(AOx) (<8.5%) or the mixture of n(AOx) and n(Cat) (<10.6%). No BAC reductions could be detected in those with n(Cat) or native AOx; the ineffectiveness of native AOx in reducing BCA further confirms the essential role of the polymer shells of ENs in protecting the core enzyme complexes from inactivation. Six hours after the alcohol gavage, the animals started to wake up; the wakeup time for the group with n(AOx-Cat) was 1-2 hours earlier than those of the other groups.

To probe liver injury associated with the alcohol feeding and administrations of ENs, plasma alanine aminotransferase (ALT) was analyzed 7 hours after the treatments. ALT was significantly increased in all alcohol-fed animals. However, in comparison with other groups, the mice with n(AOX-Cat) had a tendency of lower ALT levels (FIG. 4b). Similar results of BAC reductions were also obtained in animals via tail-vein injections (FIG. 9), confirming a versatile administration of ENs.

Above studies confirm that it is feasible to develop alcohol antidotes that effectively reduce BAC and liver injury. The significantly higher effectiveness of n(AOX-Cat) than those of n(AOx) and the mixture of n(AOx) and n(Cat) further confirms the synergic effect of the AOx and Cat confined within the ENs. In fact, oxidation of alcohol consumes molecular oxygen and releases $H_2O_2$. Catalase does not only eliminate these toxic $H_2O_2$ molecules to reduce liver damage; Catalase-mediated $H_2O_2$ decomposition also regenerates molecular oxygen, which can be rapidly fed back to the AOx owning to the close-proximity architecture.

This synergic effect alleviates local depletion of oxygen, leading to accelerated alcohol oxidation and more effective reduction of BAC. Note that, besides the $H_2O_2$ production, alcohol oxidation also generates acetaldehyde, another toxic intermediate. More effective ALT reduction and complete liver injury protection relies on effective removal of acetaldehyde. A complete protection against alcohol-induced liver injury is anticipated, when highly active ADOx becomes available for the construction of n(AOx-ADOx-Cat) triple-enzyme nanocomplexes. Nevertheless, to the best of our knowledge, this appears to be the first alcohol antidote, clearly demonstrating great potentials of using ENs for broad therapeutic applications.

In sum, this example demonstrates a design of robust enzyme architectures by precisely assembling and stabilizing multiple enzymes within a nano-space. Considering the vast library of enzymes that are currently available or are being added, novel classes of enzyme machineries could be built for broad applications beyond therapeutic applications. More importantly, though judiciously choosing building enzyme molecules and harvesting their synergic and complementary effects, this example foresees creation of novel families of enzyme machineries with programmable function beyond evolution.

Example 2: Illustrative Methods and Materials for Making and Using Artificial Enzyme Nanocomplexes (ENS) with Synergic Function This example presents more details of the materials, methods and results discussed in Example 1.

1. Materials

Reagents and solvents were purchased from Sigma-Aldrich (St. Louis, Mo.) and used as received without further purification unless otherwise noted. HeLa cells were purchased from American Type Culture Collection (ATCC). The Dulbecco's Modified Eagle Medium (DMEM) growth medium and Penicillin/streptomycin were obtained from Invitrogen (Carlsbad, Calif.). Fetal Bovine Serum (FBS) was obtained from Lonza Walkerrsville Inc (Walkerrsville, Md.). CellTitra Blue cell viability kit was purchased from Promega (Madison, Wis.). N-(3-Aminopropyl) ethacrylamide hydrochloride for production of enzyme nanocomplexes was purchased from Polymer Science, Inc. Mono-sulfo-N-hydroxy-succinimido Au-nanoparticles was purchased from NanoProbe, N.Y. Fluorescence dyes including Rhodamine B isothiocyanate and Fluorescein isothiocyanate were obtained from Sigma-Aldrich (St. Louis, Mo.). Enzymes including horseradish peroxidase, glucose oxidase, invertase and catalase were purchased from Sigma-Aldrich (St. Louis, Mo.). Male C57B6 mice were purchased from Jackson Laboratory (Bar Harbor, Me.). Alcohol liquid diet AIN76A was obtained from Dyets, Inc. Ethanol Assay Kit was purchased from BioVision (Mountain View, Calif.). H&E and fluorescent TUNEL staining kits were purchased from Roche.

Single strand DNAs (ssDNAs) used for preparing enzyme nanocomplexes were purchased from Sigma-Aldrich (St. Louis, Mo.). Their sequences were provided in Table 1 below.

| Name | Sequence |
|---|---|
| ssDNA-1 | 5'-[Phos]ATACGAATTCTAC-3' (SEQ ID NO: 1) |
| ssDNA-1' | 5'-[ThiC6]ATACGAATTCTAC-3' (SEQ ID NO: 2) |
| ssDNA-2 | 5'-[Phos]AGTAGAATTCGTA-3' (SEQ ID NO: 3) |
| ssDNA-2' | 5'-[ThiC6]AGTAGAATTCGTA-3' (SEQ ID NO: 4) |
| ssDNA-I | 5'-[Phos]ATGGTTGAGGAAGTC-3' (SEQ ID NO: 5) |
| ssDNA-II | 5'-[Phos]AGACTTCCGCTATCG-3' (SEQ ID NO: 6) |
| ssDNA-III | 5'-[AmC6T]ACGATAGCATGTGTA-3' (SEQ ID NO: 7) |
| ssDNA-IV | 5'-ATACACATTCAACCA-3' (SEQ ID NO: 8) |

[Phos] stands for phosphorylation,
[ThiC6] stands for Thiol C6 S-S, and
[AmC6T] stands for Amine C6.

2. Instruments

UV-Visible spectra were acquired with a GeneSys 6 spectrometer (Thermo Scientific). Fluorescence spectra were obtained with a QuantaMaster Spectrofluorimeter (Photon Technology International). Dynamic light scattering studies of the enzyme nanocomplexes was measured on Zetasizer Nano instrument (Malvern Instruments Ltd., United Kingdom). Transmission electron microscope (TEM) images were obtained on Philips CM120 electron microscope operating with an acceleration voltage of 120 kV. Fluorescence intensities were measured with a Fujifilm BAS-5000 plate reader. Mass spectra were acquired with an Applied and photographed with a Nikon TE2000S inverted fluorescent microscope.

3. Preparation of Enzyme Nanocomplexes (ENs)

3.1 Synthesis of DNA-Inhibitor Scaffolds

The syntheses of DNA-inhibitor scaffolds were achieved by the combination use of conjugation and self-assembly technologies. Briefly, single strand DNA was first conjugated with enzyme reversible inhibitors (or their substrate derivatives) to get a single-strand-DNA-derived enzyme inhibitor (ssDNA inhibitor). After conjugation, different kinds of ssDNA inhibitors were mixed together and heated to 37° C. for 10 min. After cooling to room temperature, ssDNA-inhibitors self-assembled with their complementary strand(s) to form the DNA-inhibitor scaffolds. Detailed synthesis schemes of the ssDNA inhibitors for horseradish peroxidase (HRP), glucose oxidase (GOx) and Invertase (Inv) are shown in the scheme below and in FIG. 5.

Schematic illustration of the syntheses of ssDNA inhibitors for HRP (a), GOx (b), and Inv (c).

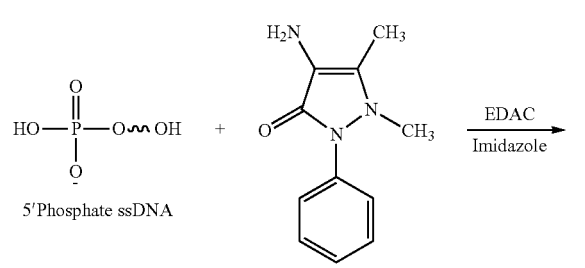

a

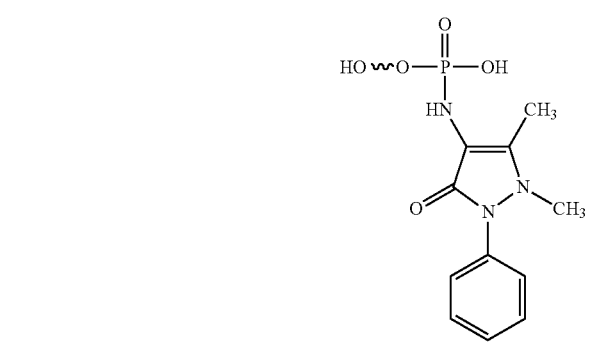

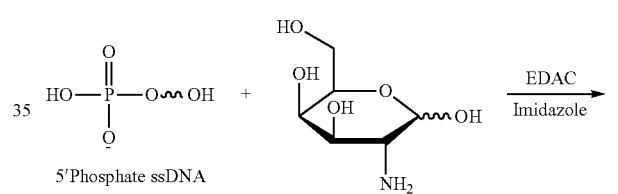

b

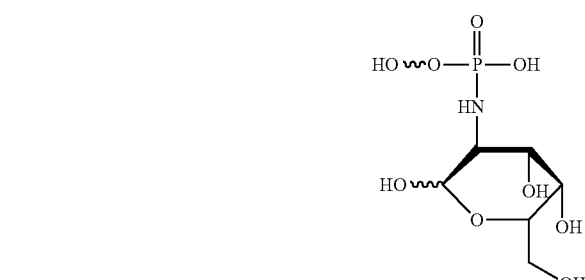

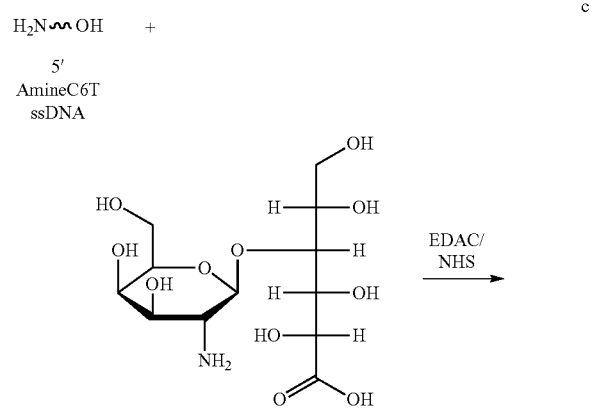

c

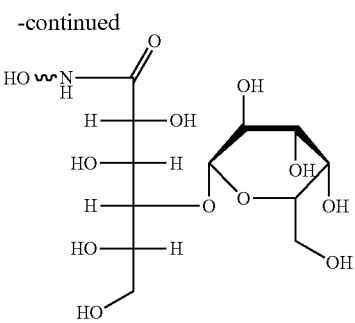

3.2 MALDI-TOF Characterizations of ssDNA-Inhibitors

Successful conjugation of ssDNA-inhibitors was demonstrated by monitoring their molecular weight increase via MALDI-TOF spectra. Ultrapure 3-hydroxypicolinic acid (3-HPA) was used as matrix for the following measurements. Unconjugated ssDNAs were used as controls for MALDI-TOF characterizations. Resulted spectra of ssDNA before (black) and after (gray) conjugating with enzyme inhibitors are shown in FIG. 6.

3.3 Synthesis of n(HRP-GOx-Inv)

n(HRP-GOx-Inv) was synthesized using a similar method as that for the preparation of n(HRP-GOx) mentioned in the Methods part. Briefly, HRP, GOx and Inv were first reacted with acrylic acid N-hydroxysuccinimide (NAS), followed by purification by dialyzing against phosphate buffer (20 mM, pH=7.2) using a dialysis tubing membrane (MWCO=10 kDa). Acryloxylated HRP, GOx, Inv, and HRP/GOx/Inv DNA inhibitor scaffold (1:1:1:5, n/n/n/n) were mixed together to form HRP-GOx-Inv enzyme complexes, and then encapsulated by in-situ polymerization on the surface of enzyme complexes. After removal of the unreacted monomers by dialysis, sample was heated to 37° C. for 10 min, followed by passing through a size exclusion chromatography (Sepharose-6B) to remove DNA-inhibitor scaffolds.

3.4 Synthesis of Dual Fluorescence-Labeled n(HRP-RhB-GOx-FITC)

Rhodamine-B-labeled horseradish peroxidase (HRP-RhB) and fluorescein isothiocyanate-labeled glucose oxidase (GOx-FITC) were prepared by following the protocol provided by the manufacturer of fluorescence dyes. Fluorescent dyes, RhB and FITC, were first dissolved in anhydrous DMSO to get 10 mg/mL stock solution. Then 50 μL of dye solutions were added gradually into 2-mg enzyme solutions (pH=8.2, sodium carbonate, 100 mM) and reacting overnight at 4° C. Labeled enzymes were purified by gel permeation chromatography (Sepharose-6B). The column was pre-equilibrated with Phosphate-Buffered Saline (PBS) and protein was eluted with the same buffer. The first color band was collected, condensed and stored at 4° C. for further use. The concentration and dye/protein ratio (D/P) of HRP-RhB and GOx-FITC were determined by the extinction coefficients of 102,000 $M^{-1}cm^{-1}$ at 403 nm (HRP), 44,100 $M^{-1}cm^{-1}$ at 280 nm (GOx) and 108,000 $M^{-1}cm^{-1}$ at 555 nm (RhB), 81,000 $M^{-1}cm^{-1}$ at 495 nm (FITC).

n(HRP-RhB-GOx-FITC) enzyme nanocomplex was prepared by using HRP-RhB, GOx-FITC as enzymes and HRP/GOx DNA-inhibitor scaffold to form enzyme complex. Detailed procedure of its preparation is the same as that of n(HRP-GOx) mentioned above. After preparation, dual fluorescence-labeled ENs were further purified by gel filtration (Superdex-75). The first band, which has a strong absorbance at 555 nm, was collected, condensed and stored at 4° C. for fluorescence characterizations.

3.5 Synthesis of Au-Nanoparticle Labeled ENs

Excess amounts of Au-nanoparticles (mono-sulfo-N-hydroxy-succinimido Aunanoparticles) were reacted with native HRP and GOx (3:1, n/n, Au/enzyme) in 1×PBS buffer for 1 hr, respectively. Excess amount of gold nanoparticles was removed by gel filtration (Superdex-75). Concentrations of the Au-nanoparticles, HRP and GOx were then determined by the UV/vis spectra based on their molar extinction coefficients (nanogold, 155,000 $M^{-1}cm^{-1}$ at 420 nm, HRP, 102,000 $M^{-1}cm^{-1}$ at 403 nm, GOx, 11,200 $M^{-1}cm^{-1}$ at 453 nm). The resulted Au-labeled HRP/GOx MCENs contain an AuNP/HRP ratio of 0.83 and AuNP/GOx ratio of 0.95.

The Au-labeled HRP and GOx were then used to prepare dual AuNP labeled ENs by using the same protocol for the preparation of n(HRP-GOx). After preparation, the sample was purified by passing through a size exclusion chromatography (Sepharose-6B), and collecting the first colored band. Sample was then stored at 4° C. for transmission electron microscopy (TEM) observation.

3.6 Synthesis of ssDNA-Alcohol Oxidase (ssDNAAOx) and ssDNA-Catalase (ssDNA-Cat) Conjugates Alcohol Oxidase (AOx) and Catalase (Cat) were dissolved in 50 mM sodium phosphate buffer (pH=7.4, 0.15 M NaCl) with a concentration of 2 mg/mL, respectively. N-succinimidyl 3-(2-pyridyldithio) propionate (SPDP) stock solution was first prepared as a 2 mM DMSO solution, followed by reacting with enzymes by gradual addition of 25 μL of SPDP solution into 1 mL enzyme solutions. Reaction was kept at 4° C. under stirring for 4 h. After the reaction was finished, mixtures were purified by gel filtration (Superdex-75) using 50 mM sodium phosphate, 0.15 M NaCl, 10 mM EDTA, pH 7.2 as eluting buffer. In the meanwhile, ssDNA-1' and ssDNA-2' were reduced with dithiothreitol (DTT) and purified by gel filtration (Superdex-75) immediately. After purification, reduced ssDNA-1' and ssDNA-2' were then added into SPD-Pactivated Cat and AOx solutions at a molar ratio of 1.2/1 (ssDNA to enzyme), respectively. The mixture was kept reacting at 4° C. overnight for a complete conjugation, and then add NAS into the mixture to anchor polymerizable sites to ssDNA-enzyme conjugates. Samples were then purified by dialysis against 1×PBS with a dialysis tubing membrane (MWCO~10 kDa) to remove unconjugated ssDNAs.

3.7 Synthesis of n(GOx-Cat) and n(AOx-Cat)

ssDNA-2-glucosamine (ssDNA inhibitor for GOx) was first mixed with equal amount of acryloxylated ssDNA-1' conjugated Cat (1/1, n/n). The mixture was heated to 37° C. for 10 min and then cooled down with an ice bath. After recovering to room temperature, in situ polymerization was carried out to encapsulate a pair of GOx and Cat into an enzyme-nanocomplex.

After removal of unreacted monomers and initiators by dialysis against 1×PBS, the sample was heated to 37° C. for 10 min and immediately passed through a size exclusion chromatography to remove ssDNA inhibitor conjugates for GOx. The first band eluted was collected and condensed to get a stock solution of n(GOx-Cat). The n(GOx-Cat) stock solution was kept at 4° C. for further use.

The preparation of n(AOx-Cat) is similar to that of n(GOx-Cat) mentioned above. Prior to polymerization, acryloxylated ssDNA-1' conjugated Cat and ssDNA-2' conjugated AOx was mixed with equal molar ratio. After polymerization, reaction mixture was purified by passing through a size exclusion chromatography to remove unreacted monomers and other by-products. n(AOx-Cat) was then condensed and aliquoted to 65 µg/tube (100 µL/tube) for in vitro and in vivo tests. Note that ENs of AOx and Cat can also be prepared by directly conjugating the both enzymes followed by a similar encapsulating technique.

4. Synthesis of Single Enzyme Nanocomplexes

Single enzyme nanocomplexes of GOx, AOx and Cat (denoted as n(GOx), n(AOx) and n(Cat)) were synthesized using the method reported in Yan et al., *Nature Nanotechnology* 5:48-53 (2010). Briefly, the enzymes were first acryloxylated by reacting with NAS, and then wrapped with a thin layer of polyacrylamine by in situ polymerization. After removal of the unreacted monomers by dialysis against 1×PBS, single enzyme nanocomplexes were then purified by passing through a size exclusion chromography (Sepharose-6B). Nanocomplexes were then collected, condensed and stored at 4° C. for further use.

5. Activity Assays and Stability of ENs 5.1 Activity Assays

Activities of enzyme complexes, n(HRP-GOx) and n(HRP-GOx-Inv), were assessed by monitoring the oxidation rate of o-Dianisidine (ODS). Briefly, a phosphate buffer (0.1M, pH=7.0) containing 0.2 mM o-Dianisidine, 500 pM of ENs and a specific amount of substrate (glucose for n(HRP-GOx) or sucrose for n(HRP-GOx-Inv)), were incubated at 25° C. for 5 min.

During the incubation, absorbance reading at 460 nm was recorded continuously with a UV/vis spectrometer. The absorption curve was plotted vs time and $\Delta A_{460}$/min from the linear portion of the curve was calculated. The activity assays were repeated with a series of appropriate concentrations of substrate to get a series of catalytic rate to obtain $K_M^{app}$ and $K_{cat}^{app}$ by the Lineweaver-Burk plot. Similar assays were also performed with free enzymes mixture (free HRP/GOx, and free HRP/GOx/Inv) as the control experiments.

TABLE 2

Kinetic parameters of HRP/GOx and HRP/GOx/Invertase free enzyme systems and their corresponding ENs

| System | $K_M^{app}$ (mM) | $K_{cat}^{app}$ s$^{-1}$ | % |
|---|---|---|---|
| Free HRP/GOx | 53.30 ± 0.44 | 244.6 ± 23.2 | 100 |
| n(HRP-GOx) | 361.85 ± 0.37 | 1262.0 ± 18.6 | 515.9 ± 7.6 |
| Free HRP/GOx/Inv | 53.30 ± 3.54 | 65.3 ± 2.5 | 100 |
| HRP-GOx- | 224.90 ± 13.64 | 1008.7 ± 61.2 | 1542.5 ± 93.5 |

Similar activity assays were also performed in polyethylene glycol (PEG, Mw-3000) solutions of a series of concentrations (0%, 5%, 10%, 15%, 20%, 25%, 30%, 35%, m/v) to simulate the viscous environment within the cells or blood stream. Briefly, certain amount of PEG was first added into phosphate buffer (0.1M, pH=7.0) to get a stock PEG solution. Then enzyme nanocomplexes (or their corresponding free enzymes mixtures) and ODS were added and mixed thoroughly to get an assay solution with an enzyme concentration of 500 pM, and ODS concentration of 0.2 mM. 145 µL of as-prepared assay solution was then passaged into a transparent 96-well plate. A series of substrates with different concentrations, which were dissolved in 5 µL of PEG solution, were then added into each well of reaction solution. Plate was then shaken for 30 s and further incubated for 5 min. Absorbance at 450 nm of each sample was then read out with a plate reader.

5.2 Thermal Stability

Solutions of n(HRP-GOx), n(HRP-GOx-Inv), free HRP/GOx mixture, and free HRP/GOx/Inv mixture were first incubated at 65° C. for certain periods (5-60 min), followed by quenching on ice bath and recovering to room temperature. Activity assays were performed with these samples to determine the residual activities of ENs and their corresponding free enzymes mixtures.

6. Transmission Electron Microscopy (TEM) Studies of ENs

Morphology and structure of ENs were examined directly by TEM. Studies were carried out on a Philips CM120 electron microscope, operating at an acceleration voltage of 120 kV. TEM samples were prepared by drop-coating of 2 µL n(HRP-GOx) solution onto the carbon-coated copper grids. Droplets of samples were contacted with grids for 45 s, then excess amount of samples were removed. The grid was then rinsed, followed by staining with 1% sodium phosphotungstate at pH 7.0.

For better imaging in TEM, silver enhancement of AuNPs was performed prior to characterization. Briefly, AuNP-labeled n(HRP-GOx) solution was first contacted with a TEM grid for 45 s. After rinsing with deionized water, the grid was floated on a drop of freshly prepared silver enhancement reagent (Nanoprobe, N.Y.) for 1 min. The grid was then rinsed again, followed by staining with 1% sodium phosphotungstate at pH 7.0. This process resulted in the formation of negatively-stained n(HRP-GOx) with 3~4 nm silver-coated AuNPs inside.

7. Dynamic Light Scattering (DLS) Studies of ENs

Figure 7:
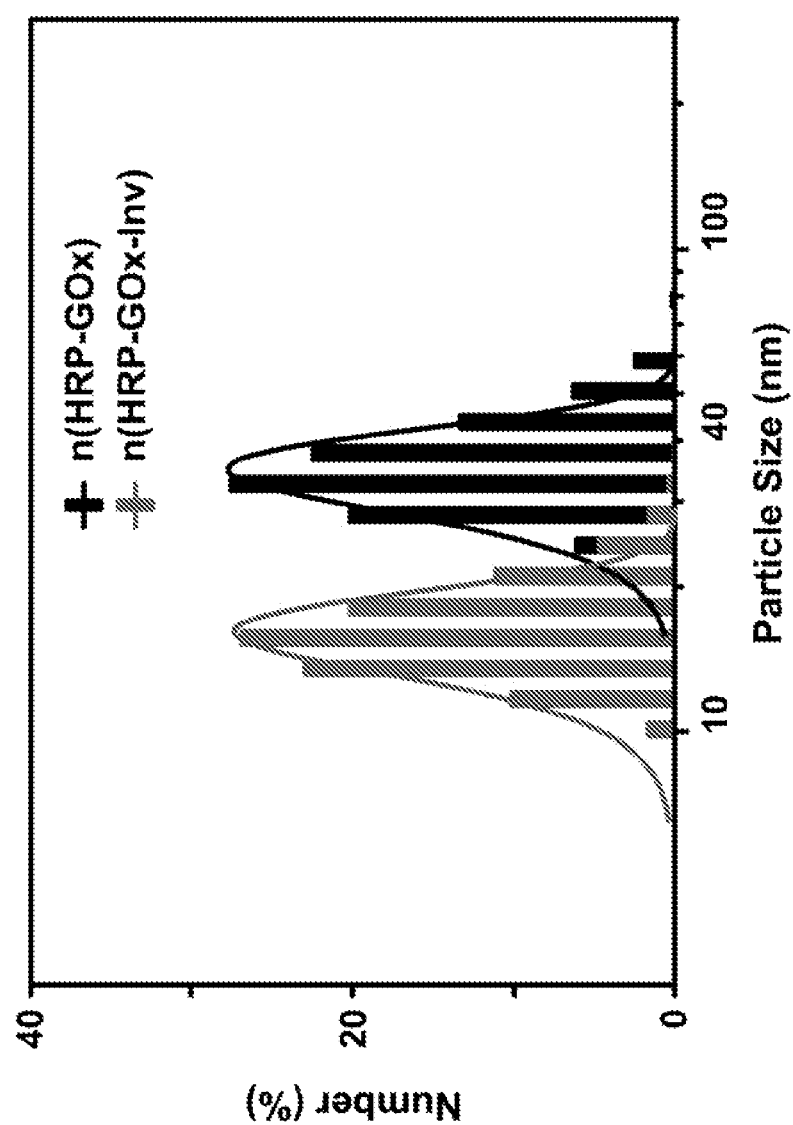
FIG. 7 presents a size distribution chart of (a) n(HRP-GOx) (gray) and n(HRP-GOx-Inv) (black).

DLS experiments were performed with a Zetasizer Nano instrument (Malvern Instruments Ltd., UK) equipped with a 10-mW helium-neon laser ($\lambda$=632.8 nm) and thermoelectric temperature controller. Measurements were taken at 90° scattering angle. Results (FIG. 7) show that the centered hydrodynamic diameters of ENs are 18±5 nm for n(HRP-GOx), and 37±8 nm for n(HRP-GOx-Inv).

8. Cell and In-Vivo Tests 8.1 Cell Viability Assay

The detoxifying capability of ENs, enzyme nanocomplex mixtures, and free enzyme mixtures was determined by cell viability assay. This study takes n(GOx-Cat), n(GOx), and a mixture n(GOx) of n(Cat) as an example. HeLa cells were seeded into a 96-well plate (10$^4$ cells/well, 100 µL/well) and cultured in DMEM (normal level of glucose in medium) for a day prior to exposure to the nanoparticles. Same amounts (0.7 mg/mL, 2 µL) of n(GOx), mixture of n(GOx) and n(Cat), and n(GOx-Cat) were then added into the wells and incubated at 37° C. for 5 h. After incubation, CellTiter-Blue (20 µL) was added into each well and further incubated for 3 h. The plate was then placed on a shaking table at 150 rpm for 5 min to thoroughly mix the solution. Viable cells reduce CellTiter Blue and show fluorescent reddish color. Quantification of the cell viability was achieved by measuring the fluorescence intensities with a plate reader (Ex=535 nm, Em=585 nm).

8.2 Analysis of the Detoxification Capability of n(GOx-Cat) in Mice

Hairs on the back of male mice (C57B6) (8~10 weeks old) were removed by an animal shaver. n(GOx-Cat), n(GOx) or n(Cat) were delivered into the skins of mice via cutaneous injection twice at 0 and 24 hours with 35 µg the enzyme (in 50 µl of PBS buffer) per injection. Equal volumes of hydrogen peroxide (H$_2$O$_2$) solution (3% w/v) and PBS buffer were injected at different spots on the back of the same animals as the positive and negative controls.

Skin damage was directly observed and recorded with a camera. The skin tissues were sectioned 48 hours after the first injection. Tissues were processed for H&E staining as previously described 2 in order to investigate the tissue damage. Fluorescent TUNEL staining was also conducted with an in-situ Cell Death Detection Kit from Roche to determine the apoptotic cell death in the skin tissue.

8.3 Cytotoxicity of n(AOx-Cat)

The toxicity of n(AOx-Cat) was assessed by a similar viability assay mentioned above, using native AOx, n(AOx), n(Cat), mixture of n(AOx) and n(Cat) as control. HeLa cells ($10^4$ cells/well, 100 µL/well) were seeded on a 96-well plate the day before exposure to the nanocapsules. Nanocapsules or native AOx (2 µg) were first incubated with the cells for 4 hrs, removed from the mixture, and incubated with fresh media. Equal amount of ethanol (3 µL) was added into each well and then incubated with cells for another 5 h at 37° C. After incubation, CellTiter Blue (20 µL) was added to each well and incubated for 3 h. The plate was then placed on a shaking table, 150 rpm for 5 min to thoroughly mix the solution. Cell viability was quantified by measuring their fluorescence intensities with a plate reader (Ex=535 nm, Em=585 nm).

8.4 In-Vivo Studies of Alcohol Antidotes and Hepatotoxicity

In-vivo studies of alcohol antidotes were achieved by monitoring the variation of blood alcohol concentration (BAC) and the level of plasma alanine aminotransferase (ALT) of mice after treating with ethanol (EtOH) and the enzyme-based alcohol antidotes. Alcohol antidote administrations were performed both orally and systematically. For systematic administration, four groups of nanocapsules were used, n(AOx), n(Cat), n(AOx)+n(Cat) mixture, and n(AOx-Cat), as well as native AOx (without nanocapsulation) used for comparison. Male C57B6 mice of 8-10 week old from the Jackson Laboratory (Bar Harbor, Me.) were used for the studies.

Mice were tail-vein injected with nanocapsules (65 µg/animal) after being fasted for 8-12 hours. Mice were then gavaged with an alcohol liquid diet (AIN76A, Dyets, Inc.) dosed at 6 g of EtOH/kg body weight (w/w) or isocaloric control at one hour after injection.

Figure 9:
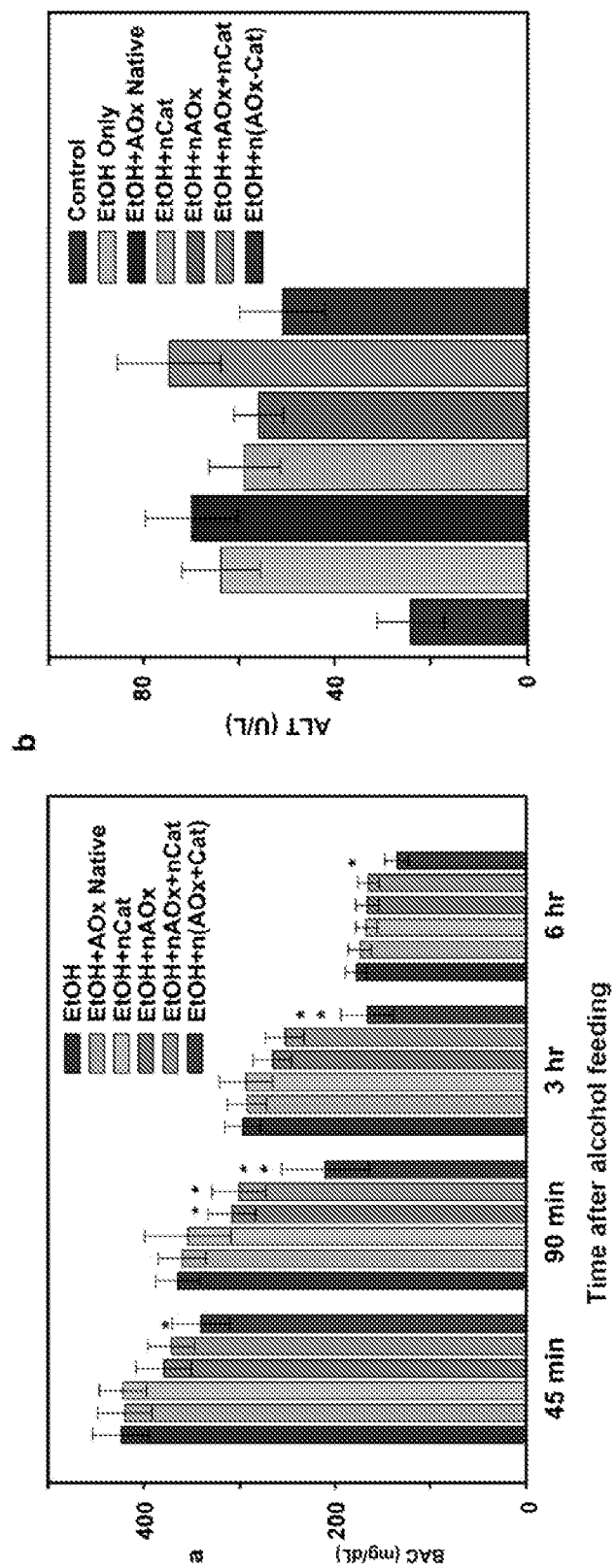
FIG. 9, similar to FIG. 4, shows that BAC reductions were also obtained in animals via tail-vein injections. (a) BAC in mice after injection of AOx containing nanocapsules (n(AOx), n(Cat), n(AOx)+n(Cat), and n(AOx-Cat)) or native AOx. For mice treated with n(AOx-Cat), BAC decreases dramatically before 3 hr (*$P<0.05$; **$P<0.01$; compared to mice fed alcohol only (EtOH); n=4 mice in EtOH-fed group). (b) ALT in mice treated by EtOH and the nanocapsules. Mice in control group were fed with normal food, other groups of mice were injected with different samples (PBS, native AOx, n(Cat), n(AOx), n(AOx)+n(Cat) mixture, and n(AOx-Cat)), followed by feeding a liquid diet containing EtOH.

BAC and ALT of mice were determined with the same methods for mice administrated orally (detailed method are described in Example 1). All animals were treated in accordance with the Guide for Care and Use of Laboratory Animals approved by local committee. As shown in FIG. 9, BAC and ALT in mice injected with n(AOx-Cat) reduced dramatically, which is consistent with the results obtained with oral administration.

Example 3: Multi-Core Enzyme Nanocapsules (MCEN) for the Acceleration of Cascade Enzyme Reactions Metabolism, happening to maintain life for all living organisms on earth, involves the millions of enzymatic cascade chemical reactions. These complicate processes, in which enzymes are dedicatedly confined in subcellular space and spatial position, allow organisms to grow and reproduce, maintain their structures, and respond to the environment. Although most of enzymes exhibiting exquisite catalytic specificity and efficiency in metabolic pathway have been well characterized and explored, successful biotransformation demonstration through multiple enzyme cascade reactions under mild conditions are still rare therefore highly attractive to scientists in chemistry biology, material and chemical engineering. An unresolved obstacle, however, is the huge reduction in the activity and stability when multiple enzymes are roughly mixed up through traditional immobilization or expressed together by whole gene cluster cloning without carefully considering their synergetic effects. The hints, shown in cases like subcellular arrangement through cellular signal anchors, compartmented polymersome, co-immobilization in mesoporous nanostructure, proved that geometry-related neighborhood, dedicated gyration control, precise ratio lock and stabilization are the key principles to the success. However, all existing designs of multiply enzyme systems, which lack homogeneity and quality control, remains rudimentary and impractical as medicine, microchip, tiny electrode and robot. We hypothesized that single-protein-leveled control through confinement and face-to face docking of several different enzymes in nanospace, the turnover rate of multistep reactions will be dramatically increased while the lifetime is fully extended.

Here we presented a highly active multi-core enzyme nanocapsules(MCEN) (Scheme 1 as shown in FIG. 1), created by integrating multiple catalytic enzymes into single small polymer nanocapsule. First, inhibitor DNA scaffold was directly fabricated by mixing four pre-designed short DNA sequences, of which three short DNA are precisely conjugated with three enzyme inhibitors (sucrose, glucosamine and 4-dimethylaminoantipyrine), respectively (Scheme 1D). Then enzyme-inhibitor complexes are formed through "key-lock" self-assembly by incubating invertase, glucose oxidase(GOx) and horseradish peroxidase(HRP) (Scheme 1A,1B,1C) with their corresponding inhibitor DNA scaffold. A very thin polymer network was coated on enzyme-inhibitor complexes through a mild in-situ polymerization to construct multi-core enzymes nanocapsule(MCEN) (Scheme 1(II)). Finally, the three-enzyme nanocapsule is obtained by removing inhibitor DNA scaffold (Scheme 1(III)). Polymer coatings in MCEN serve as artificial membranes for the encapsulated enzymes. Such artificial membranes therefore should exhibit suitable mechanical modulus to provide structural integrity, possess effective transport pathways to allow rapid substrate transport, and contain specific functionality to provide substrate selectivity. Our approach to make nanocapsules with dual- or multi-core architectures, however, allow rapid transport of reacting intermediates between the core proteins, which is of particular interest for cascade reactions.

Figure 10:
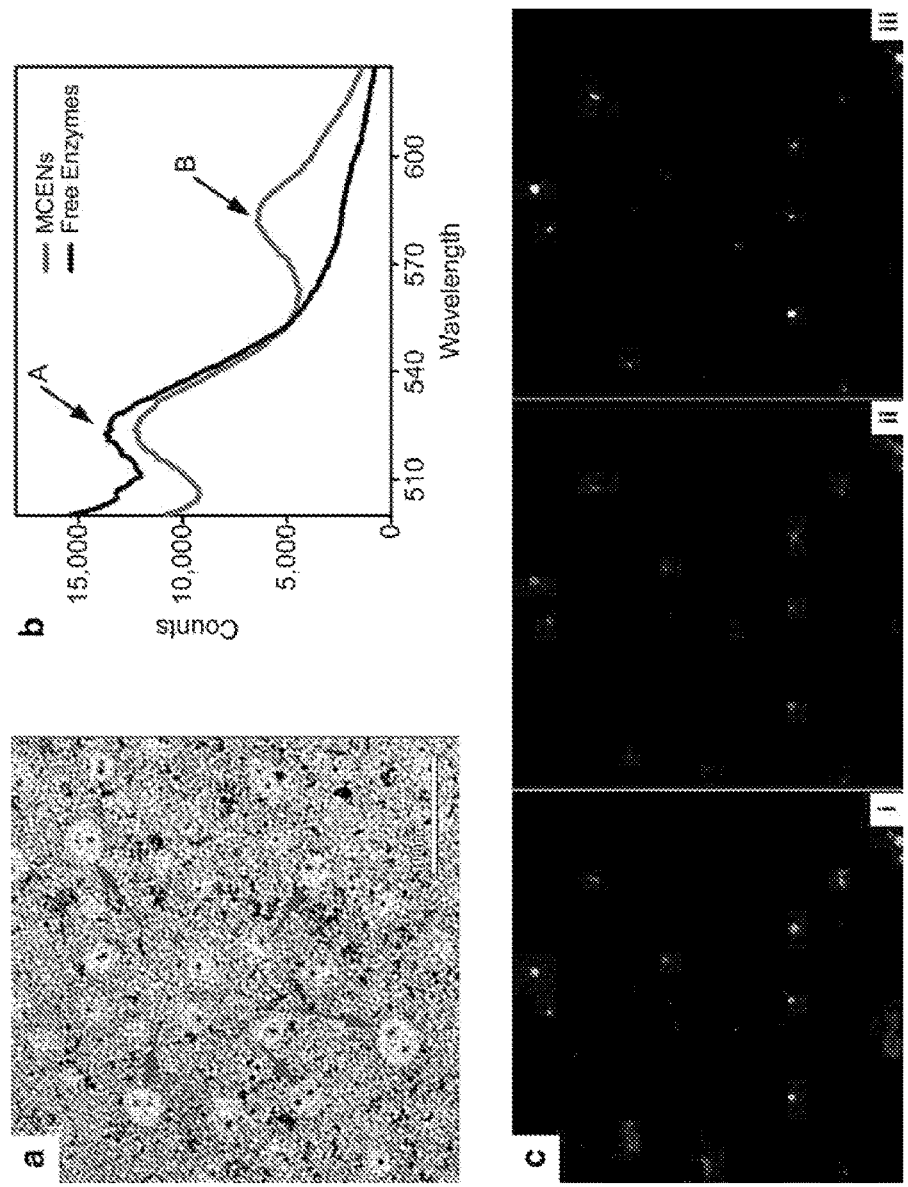
FIG. 10. Structural characterization of dual-core enzyme nanocapsule. a. TEM image of HRP-GOx dual-core nanocapsules. Both HRP and GOx were single-labelled by 1.4 nm gold nanoparticles. b. Fluorescence spectrum of HRPGOx dual-core nanocapsules including pair of dyes. The spectrum was recorded at=450 nm (corresponding the extinction wavelength of FITC) following=490~630 nm. The emission at=585 nm (peak B), which corresponds to the fluorescence of Rhodaomine B, is excited by the fluorescence of FTIC at=585 nm (peak A). c. Confocal microscopy images of HRP-GOx dual-core nanocapsules that include pair of dyes. HRP and GOx are labeled with Rhodamine B and FITC, respectively. i. Fluorescence image of GOx-FITC in dual-core nanocapsules. Image was recorded by the extinction of FITC at=450 nm following the fluorescence of FITC at 510~530 nm. ii. Fluorescence image of HRP-RhB in dual-core nanocapsules. Image was recorded by the extinction of RhB at=540 nm following the fluorescence of RhB at 570~600 nm. iii. Fluorescence image of HRP-RhB (FRET) in dual-core nanocapsules. Image was recorded by the extinction of FITC at=450 nm following the fluorescence of RhB at 570~600 nm.

Negatively stained TEM image (FIG. 10a) showed that most of HRP-GOx dual-core nanocapsules is round around 30 nm and have two dark dots inside. As both of HRP and GOx are labeled with single gold nanoparticle, respectively, we are able to speculate that most of nanocapsules only have one set of HRP and GOx inside. Fluorescence spectrum (FIG. 10b) and fluorescence confocal microscopy (FIG. 10c) was used to investigate FRET(Fluorescence Resonance Energy Transfer) effect of Rhodaomine B labeled HRP and FITC labeled GOx in nanocapsule, which reflects the spatial distance between two enzymes. There is only FITC emission peak at 520 nm (FIG. 10b) excited by blue light at 450 nm on the fluorescence spectrum, indicating there is no FRET effect between Rhodaomine B on HRP and FITC on GOx. On the contrary, there are two fluorescence emission peaks (520 nm for FITC and 585 nm for Rohamine B) excited only by blue light at 450 nm on the fluorescence spectrum of dual-core enzyme nanocapsules solution, indicating there is energy transfer from FITC to Rhodamine B. As FRET effect only happens at really short distance(<10 nm), we conclude that HRP and GOx are packaged in one nanocapsules. The dual-core enzyme nanocapsule through confocal microscopy confirmed similar conclusion as that from fluorescence spectrum and showed yellow color (FIG. 11c—iii) excited at 450 nm, which actually is mixed up by green color (FIG.

Figure 11:
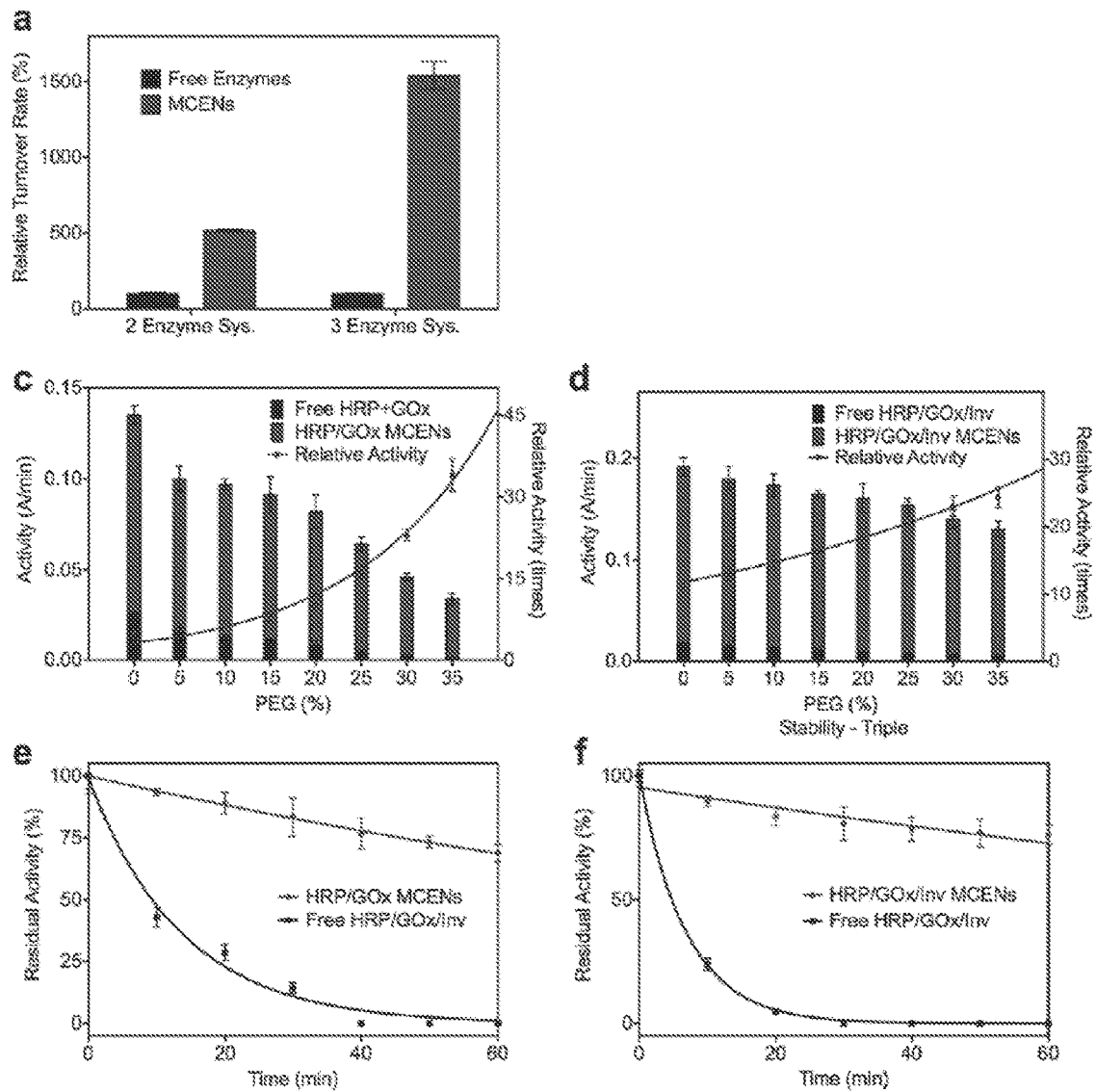
FIG. 11. Comparison of the activity and stability between multi-core enzyme nanocapsule and free enzymes system. a. Relative turnover rate of free enzymes (black) and multicore enzyme nanocapsule (red). The turnover rates of each system are determined with the oxidation rates of ODS by various concentration of substrates (glucose for two enzymes system and sucrose for three enzymes system) in the present of free enzymes (HRP/GOX for two enzymes system, HRP/GOx/Inv for three enzymes system) or multi-core enzyme nanocapsules (HRP/GOx dual-core enzyme nanocapsules and HRP/GOx/Inv triple-core enzyme nanocapsules, respectively). Both the concentration and the ratio of enzymes in free enzymes system and multi-core nanocapsules are exactly the same. All assays are performed in 100 mM phosphate buffer (pH=7.0) c. Activity comparison of three enzyme system in various concentration of PEG3000 phosphate buffer (50 mM, pH=7.0). d. [MODEL]. e & f. Thermo-deactivation of free enzyme system and multi-core enzyme nanocapsules (e. HRP/GOx, f. HRP/GOx/Inv) at 65° C.

11c—i) and red color(FIG. 11c—ii). Thus, those results suggested each dual-core nanocapsules has single HRP and single GOx inside, which are really close to each other.

We compared the activity and stability between multi-core enzyme nanocapsule and free enzymes system. Here, HRP and GOx are used as cascade reaction enzymes in dual-core enzyme nanocapsule system while Invertase, GOx and HRP are enzymes used in triple-core enzyme nanocapsule system. The turnover rates of each system are determined with the oxidation rates of ODS by various substrates (glucose for two enzymes system and sucrose for three enzymes system) in the present of free enzymes combination or multicore enzyme nanocapsules. Both the molar concentration and the ratio of enzymes in free enzymes system and multi-core nanocapsules are exactly the same. In aqueous buffer solution, enhancement of turnover rate for dual-core and triple-core enzyme nanocapsules over free enzyme system reached 460% and 1500%, respectively (FIG. 11a). Viscosity effect, which is simulated by different concentration of PEG3000, to the turnover rate of multi-core enzyme nanocapsule are also investigated, as most of cytoplasm is full of high viscosity fluid. When PEG3000 content increases, turnover rates of free multiply enzyme system and multi-core nanocapsules decrease simultaneously (FIG. 11c). But turnover rate for dual-core enzyme nanocapsule compared with free two-enzyme system is elevated from 4 fold to 34 fold when the activity assay is conducted in the 0%-35% PEG buffer solution. Similar to the two enzyme system case, triplecore enzyme nanocapsule system (Invertase, GOx and HRP) has 9 fold to 24 fold enhancement over free three enzyme system in turnover rate when PEG concentration changed from 0% to 35%. Dual-core and triple-core enzyme nanocapsules also presented a much higher stability against high temperature compared with free two and three enzyme system. After being incubated at 65° C. for 60 minutes, residual activity of dual-core and triple-core nanocapsules is 70% and 75%, respectively. At the same condition, free two and three enzyme system only have less than 2% activity left.

Figure 12:
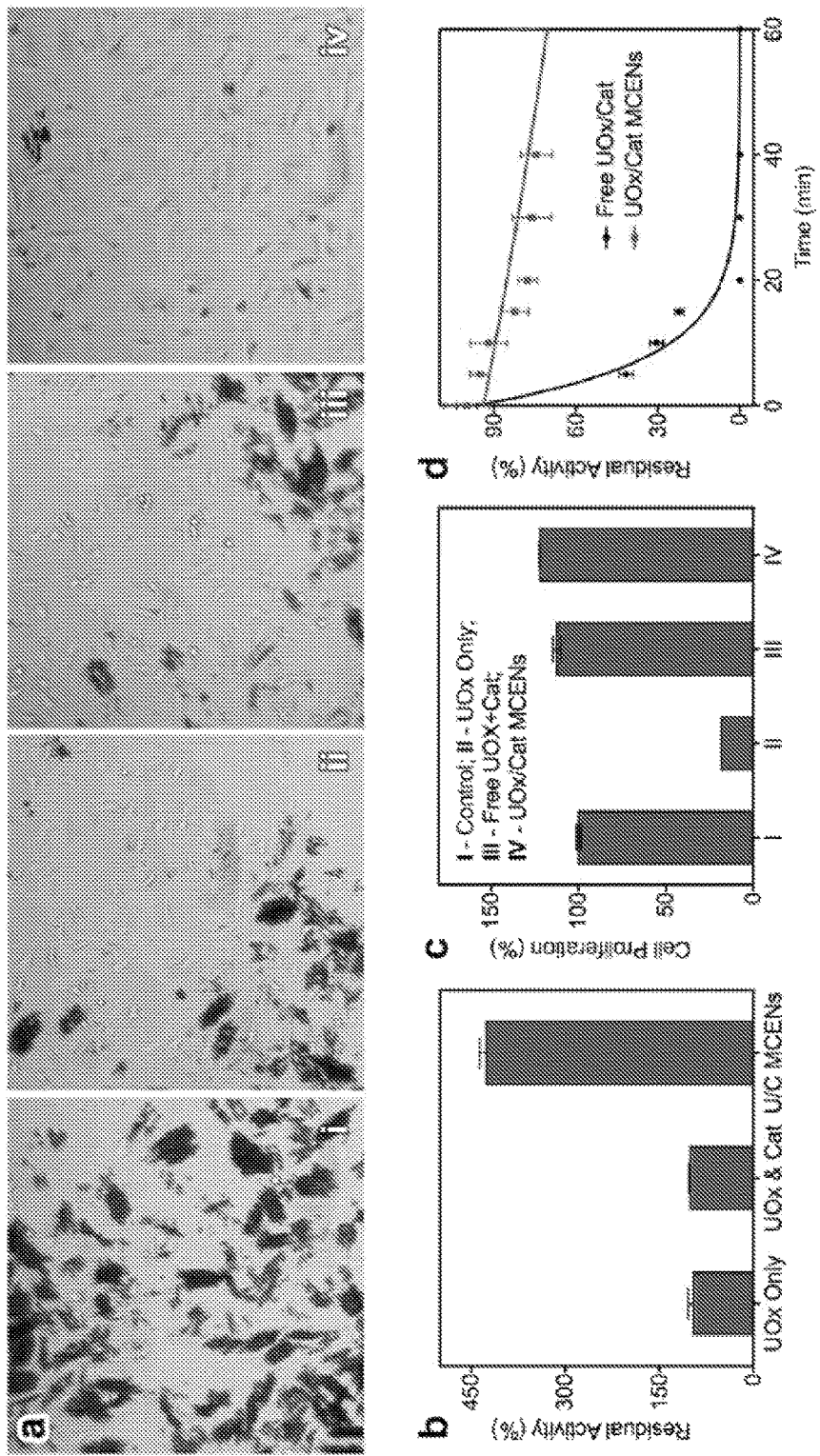
FIG. 12. a. Optical microscopy images of HeLa cells incubating at 37° C. for 2.5 h in present of uric acid (1.2 mg/mL, the black crystal in all pictures), PBS (10 μL, for control experiments, i), Uricase only (10 μL, 0.0013 mg/mL, ii), Uricase and Catalase (10 μL in total, UOx 0.0013 mg/mL, Cat 0.0026 mg/mL, iii), and Uricase-Catalase dual-core nanocapsules (10 μL, UOx 0.0013 mg/mL, Cat 0.0026 mg/mL, iv). b. Relative turnover rates of uricase only, free uricase & catalase and uricase-catalase dual-core nanocapsules. The turnover rates are determined by the oxidation of uric acid. All concentrations of uricase in each system are the same, and the concentration of catalase in free UOx/Cat system and UOx/Cat dual-core nanocapsules are also the same. c. Deactivation of free UOx/Cat system (black) and UOx/Cat dual-core nanocapsules (red) by the proteinase (trypsin). d. Cytotoxicity of UOx only system, free UOx/Cat system and UOx/Cat dual-core nanocapsules.

Uricase, a highly potential enzyme drug for gout therapy, is able to use oxygen to oxidize uric acid and generate uricate and hydrogen peroxide. Therefore, the main restraints for uricase are the low clearance efficiency of uric acid at low oxygen area or deep tissue and the heart-threaten product hydrogen peroxide. To address these issues, we build up uricase and catalase dual-core nanocapsule as a highly efficient and safe gout therapeutic drug candidate. Compared with uricase only, uricase and catalase dual-core nanocapsule achieve 400% enhancement in uric acid degradation (FIG. 12c). MTT assay showed that uricase leads to more than 75% reduction of cell viability and dualcore nanocapsule elevates cell viability to 120% due to remove of uric acid from cell culture medium (FIG. 12d). Dual-core nanocapsule still has more than 75% activity left after incubation with trypsin at 37° C. for 90 mins while activity of native uricase is less than 1% after 20 mins incubation with trypsin (FIG. 12e). Optical microscopy images represented that HeLa cells (FIG. 12a) were incubated at 37° C. for 2.5 hrs in present of uric acid crystal without uricase (FIG. 12a(i)), with uricase only (FIG. 12a(ii)), with uricase and catalase (FIG. 12a(iii)) and with uricase and catalase dual-core nanocapsules(FIG. 12a(iv)). Uricase alone was able to degrade the uric acid crystals but leads to cell death, which is indicated by the round and shrinking of cell morphology. Compared with uricase and catalase free system, uricase and catalase dual-core nanocapsules leaded to full clearance of uric acid crystal in the cell culture well without any negative effects to the cell viability. All these investigations proved that uricase and catalase dual-core nanocapsules are a highly potential efficient and safe gout therapeutic drug candidate.

We have demonstrated a revolutionarily new method to encapsulate multiply enzymes into one nanocapsules with significantly enhanced activity and stability. Precise multi-core architecture nanocapsules using DNA scaffold, allow rapid transport of reacting intermediates between the core enzymes, which is of particular importance for acceleration of cascade reactions. Moreover, judicious choice of the core enzymes allows the synthesis of nanocapsules with a wide range of cascade reactions. More generally, this study will allow the awesome power of enzyme catalysis to be harvested towards a wide range of nonphysiological applications.

Scheme Multi-Core Enzymes Nanocapsule (MCEN).

I—Self-assembly of three enzymes (enzyme A—invertase; enzyme B—glucose oxidase; enzyme C—horseradish peroxidase) and their corresponding inhibitor DNA scaffold (inhibitor a—sucrose; inhibitor b—glucosamine; inhibitor c—4-dimethylaminoantipyrine); II—Multi-core Enzymes Nanocapsule(MCEN) formed through in-situ polymerization; III—Inhibitor DNA scaffold removed from multi-core enzymes nanogel.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

The invention claimed is:

1. A multiple-enzyme nanocomplex comprising at least two different enzymes and a polymeric network which is anchored to at least one of said at least two different enzymes, wherein the multiple-enzyme nanocomplex has material properties that result from being prepared by a method comprising:
    (a) selecting a first enzyme and a second enzyme for encapsulation;
    (b) linking the first enzyme and the second enzyme to one another, wherein the linking comprises conjugating said enzymes to single nucleic acid strands that are hybridizable to each other and allowing the strands to hybridize;
    (c) acrylating the linked enzymes produced by (b);
    (d) combining the acrylated multiple-enzyme complex produced by (c) with polymerizable monomers so that the monomers are linked to the acrylated multiple-enzyme complex; and
    (e) polymerizing the polymerizable monomers and the acrylated multiple-enzyme complex in situ on the surface of the multiple-enzyme complex so as to produce a polymeric network that forms a permeable shell that encapsulates the multiple-enzyme complex.

2. The multiple-enzyme nanocomplex according to claim 1, wherein said polymeric network is anchored to all of said at least two different enzymes.

3. The multiple-enzyme nanocomplex according to claim 1, wherein the activities of said two different enzymes catalyze a cascade reaction.

4. The multiple-enzyme nanocomplex according to claim 1, wherein said at least two different enzymes are covalently or non-covalently linked to one another.

5. The multiple-enzyme nanocomplex according to claim 4, wherein the covalent linkage is degradable in vivo.

6. The multiple-enzyme nanocomplex according to claim 1, wherein said polymeric network comprises a polymer composed of at least one monomeric unit.

7. The multiple-enzyme nanocomplex according to claim 6, wherein said polymeric network comprises a polymer composed of at least two different monomeric units.

8. The multiple-enzyme nanocomplex according to claim 1, wherein the polymeric network encapsulates the multiple-enzyme nanocomplex in a manner sufficient to inhibit degradation of the multiple-enzyme nanocomplex when the multiple-enzyme nanocomplex is disposed in an in vivo environment.

9. The multiple-enzyme nanocomplex according to claim 8, wherein the multiple-enzyme nanocomplex consists essentially of two different enzymes.

10. The multiple-enzyme nanocomplex according to claim 9, wherein:
    the first enzyme generates a first product in a first enzymatic reaction with a first substrate;
    the second enzyme reacts with the first product in a second enzymatic reaction; and
    the polymeric network exhibits a permeability sufficient to allow the first substrate to diffuse from an external environment outside of the shell to the first enzyme so that the first product is generated; and
    the polymeric network exhibits a permeability sufficient to allow the first product to diffuse away from the first enzyme and to the second enzyme so that the second enzymatic reaction occurs.

11. The multiple-enzyme nanocomplex according to claim 10, wherein:
    the first enzyme is an alcohol oxidase; and
    the second enzyme is a catalase.

12. The multiple-enzyme nanocomplex according to claim 11, wherein the multiple-enzyme nanocomplex is combined with one or more filling agents, binding agents or buffering agents adapted for use in an orally administered formulation.

* * * * *

SEQUENCE LISTING

<160> NUMBER OF SEQ ID NOS: 8

<210> SEQ ID NO 1
<211> LENGTH: 13
<212> TYPE: DNA
<213> ORGANISM: Artificial Sequence
<220> FEATURE:
<223> OTHER INFORMATION: Linker

<400> SEQUENCE: 1
atacgaattc tac    13

<210> SEQ ID NO 2
<211> LENGTH: 13
<212> TYPE: DNA
<213> ORGANISM: Artificial Sequence

```
<220> FEATURE:
<223> OTHER INFORMATION: Linker

<400> SEQUENCE: 2
atacgaattc tac                                                        13

<210> SEQ ID NO 3
<211> LENGTH: 13
<212> TYPE: DNA
<213> ORGANISM: Artificial Sequence
<220> FEATURE:
<223> OTHER INFORMATION: Linker

<400> SEQUENCE: 3
agtagaattc gta                                                        13

<210> SEQ ID NO 4
<211> LENGTH: 13
<212> TYPE: DNA
<213> ORGANISM: Artificial Sequence
<220> FEATURE:
<223> OTHER INFORMATION: Linker

<400> SEQUENCE: 4
agtagaattc gta                                                        13

<210> SEQ ID NO 5
<211> LENGTH: 15
<212> TYPE: DNA
<213> ORGANISM: Artificial Sequence
<220> FEATURE:
<223> OTHER INFORMATION: Linker

<400> SEQUENCE: 5
atggttgagg aagtc                                                      15

<210> SEQ ID NO 6
<211> LENGTH: 15
<212> TYPE: DNA
<213> ORGANISM: Artificial Sequence
<220> FEATURE:
<223> OTHER INFORMATION: Linker

<400> SEQUENCE: 6
agacttccgc tatcg                                                      15

<210> SEQ ID NO 7
<211> LENGTH: 15
<212> TYPE: DNA
<213> ORGANISM: Artificial Sequence
<220> FEATURE:
<223> OTHER INFORMATION: Linker

<400> SEQUENCE: 7
acgatagcat gtgta                                                      15

<210> SEQ ID NO 8
<211> LENGTH: 15
<212> TYPE: DNA
<213> ORGANISM: Artificial Sequence
<220> FEATURE:
<223> OTHER INFORMATION: Linker

<400> SEQUENCE: 8
atacacattc aacca                                                      15
```